(12) United States Patent
Harvey et al.

(10) Patent No.: US 9,363,997 B2
(45) Date of Patent: *Jun. 14, 2016

(54) METHODS AND COMPOSITIONS FOR THE GENERATION OF PERACETIC ACID ON SITE AT THE POINT-OF-USE

(71) Applicants: Michael S. Harvey, Modesto, CA (US); Jonathan N. Howarth, Modesto, CA (US)

(72) Inventors: Michael S. Harvey, Modesto, CA (US); Jonathan N. Howarth, Modesto, CA (US)

(73) Assignee: Enviro Tech Chemical Services, Inc., Modesto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/681,938

(22) Filed: Apr. 8, 2015

(65) Prior Publication Data

US 2015/0208652 A1    Jul. 30, 2015

Related U.S. Application Data

(62) Division of application No. 14/019,296, filed on Sep. 5, 2013, which is a division of application No. 13/065,553, filed on Mar. 24, 2011, now Pat. No. 8,546,449.

(51) Int. Cl.
| | |
|---|---|
| *A61K 31/19* | (2006.01) |
| *A01N 37/16* | (2006.01) |
| *C11D 3/39* | (2006.01) |
| *C11D 11/00* | (2006.01) |
| *A01N 59/00* | (2006.01) |
| *C11D 3/395* | (2006.01) |
| *D06L 3/02* | (2006.01) |

(52) U.S. Cl.
CPC ............... *A01N 37/16* (2013.01); *A01N 59/00* (2013.01); *C11D 3/3947* (2013.01); *C11D 3/3955* (2013.01); *C11D 3/3956* (2013.01); *C11D 11/0041* (2013.01); *D06L 3/025* (2013.01)

(58) Field of Classification Search
USPC ........................................................ 514/557
See application file for complete search history.

(56) References Cited

U.S. PATENT DOCUMENTS 8,546,449 B2 * 10/2013 Harvey ................ C11D 3/3947
514/557

* cited by examiner

*Primary Examiner* — Rei-Tsang Shiao
(74) *Attorney, Agent, or Firm* — Audrey A. Millemann; Weintraub Tobin

(57) ABSTRACT

Methods for the generation of non-equilibrium solutions of peroxyacetic acid are disclosed. These methods comprise introducing triacetin sad aqueous hydrogen peroxide to water, mixing, and then adding an aqueous source of an alkali metal or earth alkali metal hydroxide. Triacetin is converted rapidly and with a high conversion rate into peracetic acid. These methods produce solutions with a high level of peracetic acid.

14 Claims, 1 Drawing Sheet

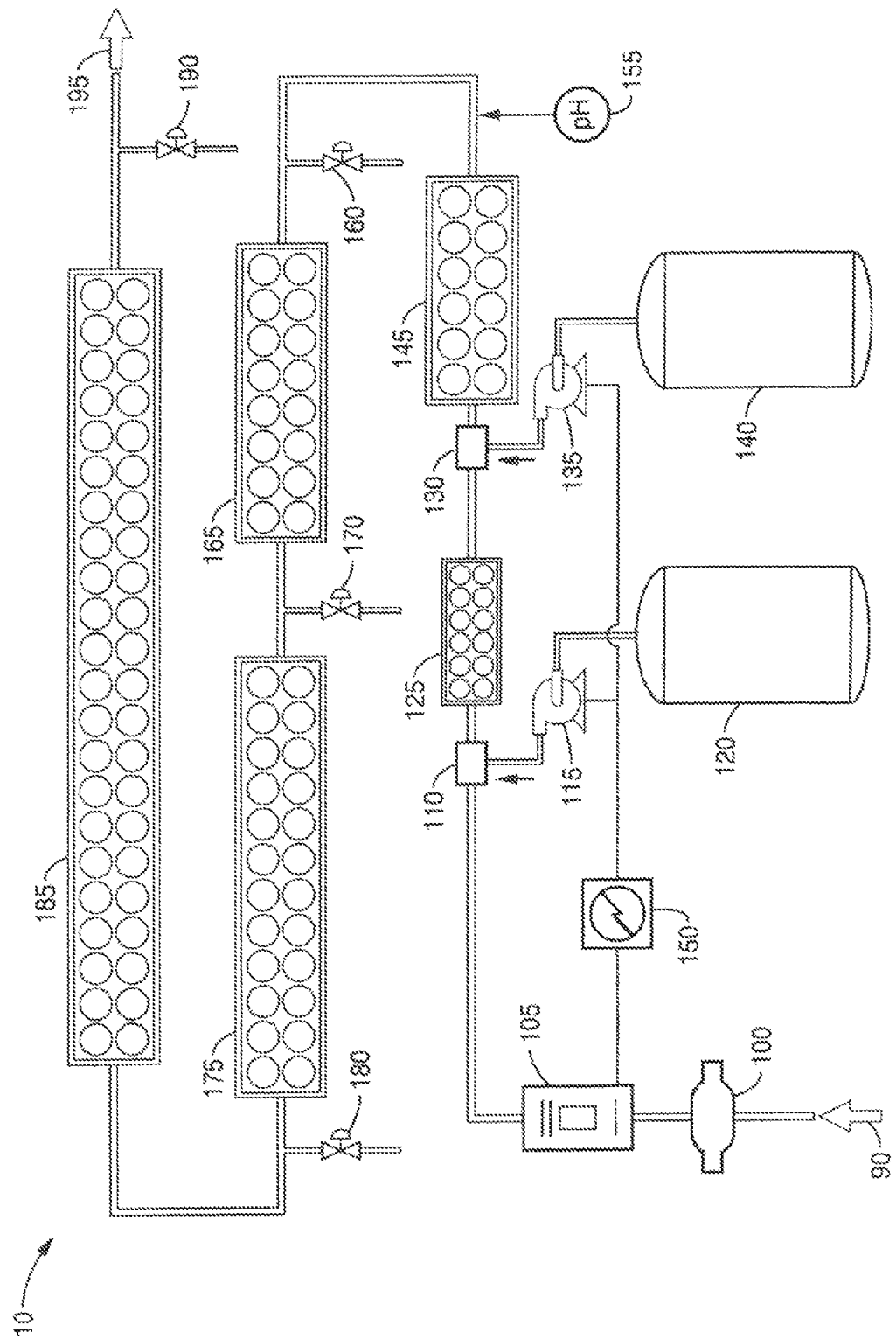

METHODS AND COMPOSITIONS FOR THE GENERATION OF PERACETIC ACID ON SITE AT THE POINT-OF-USE

CROSS REFERENCE TO RELATED APPLICATIONS

This is a divisional application of co-pending U.S. patent application Ser. No. 14/019,296 filed on Sep. 5, 2013, which is a divisional of prior application Ser. No. 13/065,553 filed on Mar. 24, 2011, now U.S. Pat. No. 8,546,449 issued on Oct. 1, 2013, pursuant to 35 U.S.C. §§120 and 121, and hereby incorporates both applications by reference in their entirety.

FIELD OF INVENTION

The invention relates to liquid compositions and methods of using the liquid compositions for the generation of a peroxyacetic acid sanitizer on site in proximity to the point-of-use. The invention also relates to a solid bleaching and stain removal composition.

A. Liquid PAA Disinfectants and Sanitizers

This is a divisional of prior application Ser. No. 14/019,296 filed on Sep. 5, 2013. Disinfectants and sanitizers based on peroxyacetic acid (PAA), also commonly known as peracetic acid, are used in the dairy, food and beverage processing industries for clean-in-place pipeline and equipment disinfecting and cleaning, for fruit and vegetable washing, and in the treatment of meat, poultry and seafood products. Peroxyacetic acid disinfectants are also used in the treatment of cooling water, process water, and municipal wastewater. Other uses include slime and biofilm removal in papermaking processes.

Peroxyacetic acid products are supplied as stable equilibrium ternary aqueous solutions of peroxyacetic acid, acetic acid, and hydrogen peroxide. They are prepared in advance of delivery, typically by reacting hydrogen peroxide with acetic acid in the presence of a mineral acid catalyst. Although some PAA is formed immediately, the PAA does not reach its maximum concentration until after several days. A metal chelating agent, such as hydroxyethylidene diphosphonic acid (HEDP) or dipicolinic acid, is also introduced to suppress the transition metal cation catalyzed decomposition of peroxygen compounds. The PAA product is then placed in containers, such as totes, drums and pads, in preparation for shipment to the end user. Typical commercial products have concentrations of PAA of about 1-15% w/w, although a concentration of up to 30% is possible. However, the latter concentration product only finds captive use because of its extremely hazardous and explosive properties.

There are several problems with the use of equilibrium solutions of PAA. First, the low concentration of PAA (1-15%) means that most of the weight (85-99%) of the products consist of substantial amounts of inert ingredients, such as water, acetic acid, and hydrogen peroxide. This results in the need for larger product storage areas and causes increased transportation and handling costs. Second, the products are inefficient in the use of both hydrogen peroxide (hydrogen peroxide) and acetic acid (AA). To maintain adequate storage stability of the PAA, either hydrogen peroxide or AA must be present at a level on a weight percentage basis that is greater than the level of PAA, which increases raw material costs. Third, the presence of the HEDP or dipicolinic acid stabilizer limits the amount of PAA that can be applied to certain foodstuffs because the amount of HEDP or dipicolinic acid is regulated by the Food acid Drug Administration (FDA). Fourth, the reaction between hydrogen peroxide and AA is quite slow in some cases, and typically requires several days' time before the PAA product can be tested for quality confirmation. Therefore, manufacturers of these products must store large inventories of the PAA product before it can be shipped to the end user. Fifth, for transportation purposes, equilibrium solutions that are greater than 6% PAA are considered to be dangerous products and must be labeled with the DOT marking "Organic Peroxide", Hazard Class 5.2, 8 (oxidizer, corrosive). If producers and end-users exceed the yearly threshold amount of just 6,666 lbs. of 15% PAA, they must file Risk Management Plans with both federal EPA and state Authorities. This is an arduous and time-consuming process. In addition, producers of equilibrium solutions of PAA that are over 6% PAA must obtain permitting by the local fire department and pay an extra hazardous material shipping fee when the product is shipped from their facility. On the other hand, there are much less stringent requirements for products that contain hydrogen peroxide, and all reporting, permitting and shipping restrictions are lifted for products that contain less than 27% hydrogen peroxide.

As a result of these problems, there have been various attempts to make non-equilibrium solutions of PAA on site, at the point-of-use. For example, U.S. Pat. No. 7,012,154 discloses a system in which AA, hydrogen peroxide, water, and sulfuric acid are fed to a jacketed reactor for the production of PAA. A wiped-film distillation column attached to the reactor condenses and isolates the pure PAA from the gas phase and immediately introduces it to the receiving water. This system suffers from a number of drawbacks. First, it is extremely capital intensive due to the high cost of the equipment, including the reactor, heater, pumps, distillation column, and computerized control system which ensures accurate metering of the reagents. Second, there are significant safety hazards associated with the production of pore PAA due to its explosive properties. Third, the equipment and synthesis process is very complex and requires knowledgeable and highly trained technicians to continuously operate and maintain the system in a safe and effective manner.

Other attempts to make non-equilibrium solutions of PAA at the point-of-use are based on electrolytic processes. U.S. Pat. No. 6,171,551 and 6,387,236 disclose processes that employ a cell divided by an ion-exchange membrane in which PAA (and other oxidants including hydrogen peroxide and ozone) are produced in the anode compartment which consists of an aqueous solution of acetic acid or acetate salt. In addition to the high costs of electricity and electrolysis equipment, these processes also result in a very low yield of PAA from the acetyl precursor. For example, the '551 patent reports that less than 14 ppm of PAA was produced alter 90 minutes of electrolysis of a 490,000 ppm anolyte of aqueous potassium acetate. In addition, these processes are difficult to perform intermittently.

Other methods of generating non-equilibrium solutions of PAA on site, using electrolysis, are described in WIPO International Publication Nos. WO 2004/0245116 and WO 2008/140988, and U.S. Patent Application Publication No. 2009/0314652. These references disclose cation membrane-divided electrolysis cells and the use of gas diffusion electrodes to effect the cathodic reduction of oxygen gas to hydrogen peroxide under alkaline conditions. The hydrogen peroxide was then allowed to react with acetic acid or an acetyl precursor to form PAA in the bulk solution, whereupon the catholyte was directed to the acidic anode compartment of the cell to stabilize the PAA. This system suffers from several disadvantages. Due to the low solubility of oxygen in water (about 8 ppm maximum), the concentration of electroactive species is very low, which forces the cell to operate at low current density (amperage per surface area of electrode). In order to produce a meaningful amount of hydrogen peroxide, the cells must have a very large surface area. This requires high capital equipment costs and a very large footprint for the electrolysis equipment. Another disadvantage of this system is that it is very difficult to maintain steady-state conditions and simultaneously balance the feed of acetic acid or acetyl precursor to the cathode compartment with the concurrent withdrawal of acidified PAA solution from the anode compartment. This is because cations carrying the cell current through the cation exchange membrane are always hydrated so as the cations move through the membrane, they are accompanied by water molecules. As a result, the volume of the anolyte decreases and the volume of the catholyte increases, making the steady-state condition difficult to maintain. It is difficult to perform this process intermittently. Finally, this system can only be of economic value if the source of oxygen is air, which comprises 23% oxygen. However, the carbon dioxide contained in air causes carbonates to precipitate, which Impedes the flow of electrical current, limiting or eliminating the production of hydrogen peroxide, and hence, PAA.

Another method of making a non-equilibrium solution of PAA at the point-of-use is disclosed in WIPO International Publication No. WO 2008/140988 and U.S. Patent Application Publication Nos. 2009/0005590 and 2007/0082832. These references disclose biosynthetic methods of producing peracids from carboxylic acids and carboxylic acid esters. These methods involve the use of perhydrolase enzymes to catalyze the perhydrolysis of the carboxylic acid or ester into the peracid using a solid or liquid source of hydrogen peroxide. Although these methods can produce compositions containing up to 20 parts of peracid to one part of hydrogen peroxide, they are limited by the amount of peracid that can be produced before the perhydrolase enzyme is oxidized by the reactant products and ceases to function as intended. The highest concentration of peracid disclosed by these references was 0.16% (1,600 mg/L). However, peracid or PAA solutions that are produced with enzymes have limited appeal because they are very expensive to produce, and for regulatory reasons, the enzyme must be removed from the solution before the solution can be applied to food or hard surfaces for disinfection purposes. Removing the enzyme from the solution is not an easy task; thus, it is typically not done. Therefore, PAA solutions prepared by enzymatic methods are not suitable for the more broad commercial uses in the food, dairy, beverage, meat, and poultry industries, which are regulated by the FDA and the Environmental Protection Agency (EPA).

Another method of generating non-equilibrium PAA at its point-of-use requires substituting the traditional mineral acid catalyst with sulfonic acid ion-exchange resins, as disclosed in U.S. Pat. No. 5,122,538. A solution containing a 1.5:1 mole ratio of AA to hydrogen peroxide was passed through a column packed with a sulfonic acid ion-exchange resin and produced a solution of 15% PAA within 30 minutes. The method described in the '538 patent suffers from the limitation that it requires a large volume of expensive resin bed in order to be effective. Moreover, all existing ion exchange resin systems are limited by the fact the resin is subject to oxidative degradation by PAA and have a short limited lifespan.

Other attempts to produce non-equilibrium PAA solutions on site, at the point-of-use, for bleaching cellulosic materials have reacted hydrogen peroxide with acetic anhydride. For example, U.S. Pat. No. 3,432,546 discloses a process where hydrogen peroxide, acetic anhydride, and an ammonium hydroxide catalyst were metered to a tubular reactor to continuously produce a solution containing 3.25% PAA with a conversion of 78% hydrogen peroxide. However, the process generated measurable amounts of diacetyl peroxide (0.44%) which is an explosion hazard. Moreover, the reaction product would be unsuited for any application other than cellulosic bleaching purposes because there was no attempt to remove the ammonium hydroxide catalyst from the reaction medium. Ammonium hydroxide is an undesirable contaminant in PAA products that are used as disinfectants and sanitizers in the dairy, food, and beverage processing industries, and in PAA products used in fruit and vegetable washing acid in the treatment of meat, poultry, and seafood.

Another process for generating non-equilibrium solutions of PAA on site, at the point-of-use was disclosed in U.S. Patent Application Publication No. 2009/0043132. This process utilized introduction of hydrogen peroxide into a sidestream of the water requiring treatment. This was followed by introducing acetic anhydride, whereupon PAA was generated in-situ. It was found that acetic anhydride preferentially reacted with hydrogen peroxide rather than undergo undesirable hydrolysis with water. Within 20 minutes, up to 3000 ppm of PAA was generated in the sidestream which was then reconstituted with the main body of water and diluted further. All processes that employ acetic anhydride suffer the limitation that acetic anhydride is expensive, very corrosive, an irritant, and highly flammable.

Yet another process for generating non-equilibrium solutions of PAA on site at the point-of-use is disclosed in WIPO International Publication No. WO 01/46519 A1. This process utilized the metering of an aqueous solution of hydrogen peroxide into an agitated tank and co-metering a solid dry source of tetraacetylethylenediamine (TAED) from a storage-hopper using a screw feeder. The agitator kept the solid TAED suspended in the hydrogen peroxide solution which was then fed to an in-line static mixer where aqueous sodium hydroxide was introduced. The mixture was then directed through 200 meters of coiled tubing immersed in a cooling tank so that the temperature rise accompanying the exothermic reaction was contained. Upon exiting the coiled tubing, the mixture containing PAA could be directed to the water requiring treatment. Disadvantages of this approach include the difficulty of accurately metering a solid and a liquid simultaneously, and the high capital equipment cost of the metering system, electronic controllers, agitation tank, coiled tubular reactor, and the cooling system.

Thus, there is a need for a method to make non-equilibrium PAA on site at the point-of-use that addresses the above problems.

B. Solid PAA Bleaches and Stain Removers

PAA is also used in laundry bleaching applications where it is generated in-situ in the laundry wash water. The PAA is typically produced from a solid source of hydrogen peroxide, such as sodium percarbonate or sodium perborate. The hydrogen peroxide must be in the presence of a solid acetyl precursor, most typically, tetraacetyletbylenediamine (TAED). When dissolved in laundry wash water, the TAED undergoes a perhydrolysis reaction with hydrogen peroxide to form PAA. TAED is the preferred acetyl precursor because it possesses low toxicity, is of low environmental impact, and is readily biodegradable. However, TAED-based laundry bleaches have several problems. First, of the four acetyl groups on TAED, only two are known to be available for perhydrolysis, making TAED an expensive acetyl precursor on a weight basis. Second, TAED has low water solubility, especially at the cooler water temperature bleaching cycles that are less damaging to fabrics. This is a major drawback, as current consumer trends in energy conservation are towards bleaching laundry fabrics with cool temperature water, rather than heated water. Undissolved TAED in cool temperature water is less unavailable as an acetyl precursor tor the dissolved source of hydrogen peroxide and can even deposit on fabrics, necessitating a separate rinse step to remove it. Third, over time, when exposed to high humidity, solid TAED can react with the solid source of hydrogen peroxide and the free water to form PAA, as well as degrade the activity, making it less effective over time. Because tile PAA is volatile. It imparts an undesirable pungent odor to the product. Thus, there is a need for a solid, peroxygen bleach that overcomes the deficiencies of the TAED-containing bleaches.

SUMMARY OF THE INVENTION

In an embodiment, liquid compositions for use in generating non-equilibrium solutions of PAA are provided. These hydrogen peroxide-acetyl precursor solutions comprise a solution of aqueous hydrogen peroxide, a liquid acetyl precursor that is soluble in aqueous hydrogen peroxide, a trace amount of peracetic acid, and water. A preferable acetyl precursor is triacetin, which displays an unexpectedly high sol ability in hydrogen peroxide. These hydrogen peroxide-acetyl precursor solutions may be used for generating a non-equilibrium solution of peracetic acid for use as a disinfectant or sanitizer on a site having a point-of-use of peracetic acid.

The hydrogen peroxide-acetyl precursor solutions are advantageous in that they are formulated such that sufficient acetyl precursor can be dissolved in an amount of hydrogen peroxide that would fully perhydrolyze all of the acetyl groups of the acetyl precursor. Moverover, the hydrogen peroxide component of these compositions is remarkably stable. These compositions overcome one or more problems of the known prior art, and are free of the regulatory reporting, permitting, and shipping restrictions that govern equilibrium PAA products.

In another embodiment, a method of preparing a hydrogen peroxide-acetyl precursor solution is provided. The method comprises introducing a liquid acetyl precursor that is soluble in aqueous hydrogen peroxide to a solution of aqueous hydrogen peroxide; and allowing the acetyl precursor and the aqueous hydrogen peroxide to mix to form a hydrogen peroxide-acetyl precursor solution.

A further embodiment is a method of continuously or intermittently generating a non-equilibrium solution of peracetic acid on a site having a point-of-use of peracetic acid for use as a disinfectant or sanitizer. Water is provided on the site having the point-of-use. The water may be a flowing aqueous stream or it may be contained in a mixing tank or other vessel. A hydrogen peroxide-acetyl precursor solution is provided on the site having the point-of-use. In one embodiment, the liquid acetyl precursor is triacetin and the solution that is formed is a hydrogen peroxide-triacetin solution. The hydrogen peroxide-acetyl precursor solution may be prepared off site and then transported to the site having the point-of-use, or the acetyl precursor and the aqueous hydrogen peroxide may be transported to the site having the point-of-use and then used to prepare the hydrogen peroxide-acetyl precursor solution on the site. The hydrogen peroxide-acetyl precursor solution is then introduced to the water. Alternatively, and in another embodiment, the acetyl precursor and the aqueous hydrogen peroxide may be introduced to the water separately, either sequentially, with either one first, or simultaneously. The hydrogen peroxide-acetyl precursor solution and the water are mixed to form a mixture. An aqueous source of an alkali metal or earth alkali metal hydroxide, such as sodium hydroxide, is provided on the site having the point-of-use. The aqueous source of an alkali metal or earth alkali metal hydroxide is added to the mixture. Alternatively, and in another embodiment, the aqueous source of alkali metal or earth alkali metal hydroxide may be added simultaneously with the hydrogen peroxide-acetyl precursor solution or with the acetyl precursor and the aqueous hydrogen peroxide, to the water. A reaction medium comprising a non-equilibrium solution of peracetic acid is formed. In the reaction medium, the hydrogen peroxide reacts with the acetyl precursor to form peracetic acid. Almost instantaneously, a non-equilibrium solution of PAA is formed. Within about 30 seconds to about five minutes, the amount of hydrogen peroxide and acetyl precursor that are converted into peracetic acid is maximized. When triacetin is used as the acetyl precursor and assuming all three acetyl groups are reacted, about 40.9% to about 85.7% of the triacetin is converted into peracetic acid, and the percent of hydrogen peroxide remaining is about 0.078% to about 1.88%. The reaction medium may optionally be sampled at various times after the addition of the aqueous source of alkali metal or earth alkali metal hydroxide to determine the time required to maximize the amount of hydrogen peroxide and acetyl precursor that are converted into peracetic acid.

The non-equilibrium solutions of PAA that are farmed comprise PAA, unreacted hydrogen peroxide, unreacted acetyl precursor, the product of the perhydrolysis reaction of the acetyl precursor, the aqueous source of alkali metal or earth alkali metal hydroxide, and water. The peracetic acid solutions are alkaline, having a pH of about 11.2 to about 13.37. The reaction is remarkably fast, proceeds with a high conversion of the acetyl precursor into PAA. This method produces solutions with a high level of PAA, from about 1% to about 7.1%.

The PAA solution is introduced to the receiving water at the point-of-use. It may be introduced immediately, of stabilized with the addition of a source of acid and used throughout a working day. The receiving water may be water used in the dairy, food, and beverage processing industries for clean-in-place pipeline and equipment cleaning; for fruit and vegetable washing; and in the treatment of meat, poultry, and seafood products. The receiving water may also be cooling water, oil and gas process water, or municipal wastewater. Other uses include slime and biofilm removal in papermaking processes.

This method addresses one or more: problems of the known prior art. The method is easy to perform, inexpensive to operate, and requires only basic and common equipment. The method is safe, in that it does not isolate pure PAA, and there is no possibility of a catastrophic event due to an equipment failure, such as over-pressurization or explosions. When triacetin is used as the acetyl precursor, it is inexpensive, non-toxic, safe, non-corrosive, non-irritating, non-flammable, sanctioned as Generally Recognized as Safe (GRAS) by the FDA, and converted quickly and with a high conversion rate into PAA. The method does not require the use of perhydrolase enzymes, acetic acid, or acetic anhydride, all of which suffer from the aforementioned limitations and problems. The method generates a PAA product that does not contain ammonium hydroxide. The method can be performed to generate a PAA product in a continuous or intermittent fashion. Further, the method allows the end-user the choice of utilizing the on site generated PAA immediately or later over the coarse of a working day.

In another embodiment, a freely-flowable, solid peroxygen composition for use in laundry bleaching and stain removal is provided. The solid composition comprises a liquid acetyl precursor, a water-soluble solid source of hydrogen peroxide, and a water-soluble: solid source of alkalinity. The liquid acetyl precursor is preferably triacetin The composition produces peracetic acid upon being introduced to water. Upon dissolution, the solid hydrogen peroxide source releases hydrogen peroxide and the solid source of alkalinity dissolves to increase the pH, resulting in the formation of peracetic acid from the reaction, of the hydrogen peroxide and the acetyl precursor.

The solid composition is used as a bleaching agent and a stain remover for the treatment of articles such as fabrics, dentures, textile garments, and equipment used in the food and beverage industry. The solid composition is advantageous in that it does not give rise to an undesirable PAA odor upon storage, contains an acetyl precursor that efficiently utilizes the acetyl groups it contains, and has a high solubility in cool temperature water which quickly and efficiently produces PAA without the need for elevated water temperatures. Moreover, the acetyl precursor used in making the solid composition may also be used in preparing the liquid compositions described in section 3 above, streamlining manufacturing practices by using the same acetyl precursor as an ingredient in liquid as well as solid compositions.

Surprisingly, this freely-flowable, solid composition includes a liquid acetyl precursor, triacetin. In addition, it is surprising that this composition does not produce a strong odor of peracetic acid during storage.

In another embodiment, a method of preparing the freely-flowable, solid peroxygen composition for use in laundry bleaching and stain removal is provided.

BRIEF DESCRIPTION OF THE DRAWING

FIG. 1 is a schematic representation of an example of a system that, may be used to continuously or intermittently generate PAA for on a site having a point-of-use of peracetic acid In another embodiment, a freely-flowable, solid peroxygen composition for use in laundry bleaching and stain removal is provided according to an embodiment.

DETAILED DESCRIPTION OF THE INVENTION

1. Definitions

The terms "PAA" and "peracetic acid" mean peroxyacetic acid or peracetic acid, and/or the conjugate base of peracetic acid (the peracetate ion).

The terms "percent" and "%" mean weight percent, except when referring to the percent converted.

The term "receiving water" means the water that is being treated.

The term "point-of-use" means the location where the peracetic acid enters the receiving water.

2. Experimental Methods

PAA and hydrogen peroxide in solution were determined using the ceric sulfate-sodium thiosulfate method. The method involves adding a known weight of sample containing the PAA and hydrogen peroxide (or dilution) to a beaker containing 50 ml of chilled 0.9 N sulfuric acid. Using a transfer pipette, 1-2 grams is accurately weighed to a sample cup and reverse osmosis (RO) or deionized water is added to provide a workable volume. Five drops of ferrous indicator is then added with stirring, and the sample is then titrated with 0.1 N ceric sulfate until the sample turns from purple to blue. The volume of ceric sulfate required in mL is recorded. Then, one or two small scoops of potassium iodide are added to the sample cup, which turns the solution dark brown. The sample is then titrated with 0.1 N sodium thiosulfate to discharge the brown coloration and form a pale straw coloration. Then, 10-15 drops of 0.5% starch indicator solution is introduced and the sample turns blue-black. The sodium thiosulfate is then added dropwise until the color transitions to a bright orange. The volume of sodium thiosulfate in mL was recorded. The percent hydrogen peroxide and the percent PAA are calculated as follows:

$$\% \text{ hydrogen peroxide} = \frac{\text{mL } 0.1\text{N ceric sulfate} \times 0.17}{\text{wt. sample}}$$

$$\% \text{ PAA} = \frac{\text{mL } 0.1\text{N sodium thiosulfate} \times 0.38}{\text{wt. sample}}$$

For kinetic runs which involved measuring the PAA and hydrogen peroxide in samples at one, three, and five minute intervals after adding the reactants together, the generation reaction was quenched by adding a sample of the reaction medium to the sulfuric acid. This halted the generation reaction and stabilized the PAA and hydrogen peroxide to elevated pH degradation reactions. This permitted the samples to be taken at the appropriate time interval (one, three, and five minutes), and analyzed later.

In circumstances where low concentrations of PAA were used, the modified DPD method (U.S. Pat. No. 7,651,724) was employed. This analytical technique is based on a modified DPD (N,N-diethyl-p-phenylenediamine) colorimetric method accepted by the EPA for measuring total chlorine in drinking water and wastewater. It relies on the ability of PAA to behave like chlorine in that it rapidly and quantitatively oxidizes iodide ion ($I^-$) into iodine ($I_2$) that reacts with a color indicator (DPD), which turns the solution a shade of pink, the intensity of which is proportional to the concentration of the PAA. A colorimeter is used that is programmed to measure the intensity (absorbance) of the pink coloration and display the result in terms of ppm as $Cl_2$. A calculation converts this number into the ppm as PAA, based on the weight ratio of PAA to $Cl_2$ (76/71=1.07).

Hydrogen peroxide does not interfere with the measurement for PAA provided the analysis is completed within 30 seconds of introducing the DPD reagent. In order for the hydrogen peroxide to be measured. It must be activated by addition of a sodium, molybdate catalyst and then given time (six minutes) to react with the $I^-$ ion to liberate $I_2$. Upon addition of the DPD indicator, the intensity of the pink coloration measured by tire colorimeter is now the sum of the PAA and hydrogen peroxide concentrations expressed as ppm $Cl_2$. Alter subtracting the ppm reading obtained earlier for the contribution due to PAA, a calculation is then used to convert this number into ppm as hydrogen peroxide, and is based on the weight ratio of hydrogen peroxide to $Cl_2$ (34/71=0.479).

3. Liquid Compositions for Generating Non-Equilibrium Solutions of PAA on a Site Having a Point-of-Use In an embodiment, liquid compositions for generating non-equilibrium solutions of PAA on a site having a point-of-use of peracetic acid are provided. These solutions are referred to as "hydrogen peroxide-acetyl precursor solutions." These solutions comprise aqueous hydrogen peroxide, a liquid acetyl precursor that is soluble in aqueous hydrogen peroxide, a trace amount of peracetic acid, and water.

The hydrogen peroxide-acetyl precursor solutions are prepared by the following steps.
(a) Introducing a liquid acetyl precursor that is soluble in aqueous hydrogen peroxide to a solution of aqueous hydrogen peroxide.

Triacetin is a preferable liquid acetyl precursor and 50% hydrogen peroxide is a preferable solution of aqueous hydrogen peroxide. The triacetin is preferably added to the 50% hydrogen peroxide at room temperature. Alternatively, 70% hydrogen peroxide can be used, but It is not widely available and requires special handling and transportation. Given that the solubility of triacetin in water is only 7% at 25° C., triacetin is unexpectedly highly soluble in 50% hydrogen peroxide. It solubilizes without an exotherm (temperature increase).

The mole ratio of hydrogen peroxide:triacetin is about 2.98:1 to about 12.84:1.

(b) Allowing the acetyl precursor and the aqueous hydrogen peroxide to mix to form a hydrogen peroxide-acetyl precursor solution.

The solution is mixed until a homogenous solution has been formed. The solution is allowed to mix by diffusion or by using a mixing device that is suitable for mixing liquids together. For example, 50% hydrogen peroxide can be introduced to a batch tank equipped with an overhead agitator blade. Triacetin can then be introduced to the 50% hydrogen peroxide when the agitator is in motion so that the components are thoroughly mixed.

The solution that is formed is a hydrogen peroxide-acetyl precursor solution, which also includes varying amounts of water, depending on the formulation used. When triacetin is used as the liquid acetyl precursor, the solution that is formed is a hydrogen peroxide-triacetin solution. One such hydrogen peroxide-triacetin solution comprises about 23% to about 40% hydrogen peroxide (from 50% aqueous hydrogen peroxide), about 20% to about 52% triacetin, water, and a trace amount of PAA that is formed within the first day of preparing the hydrogen peroxide-acetyl precursor solution. The pH is about 1.46 to about 2.2 and no deliberate attempt is made to adjust the pH further.

A preferable hydrogen peroxide-triacetin solution comprises about 27.15% hydrogen peroxide (from 50% aqueous hydrogen peroxide), about 45.67% triacetin, water, and a trace amount of PAA that is formed within the first day of preparing the hydrogen peroxide-acetyl precursor solution. The mole ratio of hydrogen peroxide:triacetin is about 3.8:1.

The hydrogen peroxide-acetyl precursor solutions prepared by this method may be used to generate non-equilibrium solutions of PAA on a site having a point-of-use of peracetic acid, in the methods described in section 4 below. The hydrogen peroxide-acetyl precursor solutions may be transported in any container suitable for transporting liquids, such as plastic tote bins of 275-330 gallons, drums of 15-55 gallons, five-gallon pails, one-gallon jugs, or other containers.

Example 1

Triacetin (83.05 g) was added to 50% hydrogen peroxide solution (75 g) to form 158.05 g of a mixture. There was no evolution of gas indicating the hydrogen peroxide had decomposed to oxygen, nor was there any exotherm indicating that a chemical reaction had occurred. The solution did not turn oily or cloudy but remained clear. The solution was calculated to comprise 23.73% hydrogen peroxide and 52.55% triacetin, with the balance being water, and had a measured pH of 2.2. The mole ratio of hydrogen peroxide to triacetin was calculated to be 2.98:1. Titration of the solution immediately upon preparation yielded 24.1% hydrogen peroxide, which is within experimental error of the calculated amount of hydrogen peroxide.

This experiment showed that triacetin is remarkably soluble in 50% hydrogen peroxide. The solubility of triacetin was found to be at least 52.55%. This is surprising, given that the solubility of triacetin in water is only 7% at 25° C.

In order to test the stability of the mixture, the amount of hydrogen peroxide remaining and the amount of PAA generated was tracked for several months. The mixture was held at ambient temperature away from sources of light. Table I summarizes the data.

TABLE I

| Day # | % Hydrogen Peroxide Remaining | % PAA Generated |
|---|---|---|
| 1 | 23.79 | 0.00 |
| 29 | 23.32 | 1.28 |
| 57 | 22.56 | 2.36 |
| 92 | 21.06 | 4.22 |
| 120 | 19.54 | 6.05 |
| 134 | 18.57 | 6.87 |

Table I shows that although there was a steady depletion in hydrogen peroxide, it was accompanied by an increase in PAA. By the end of the 134-day study, the composition had lost 5.22% hydrogen peroxide. Had all of the depleted hydrogen peroxide gone towards the generation of PAA, 11.67% PAA would have been generated. Because 6.87% PAA was generated, unaccounted losses of hydrogen peroxide amounted to 2.15%. This loss of hydrogen peroxide was surprisingly small given that hydrogen peroxide is often used to destroy organic compounds by oxidation and the composition originally contained 52.55% of triacetin, an organic compound.

Example 2

A formulation containing hydrogen peroxide and triacetin in a mole ratio of 12.84:1 was prepared by adding triacetin (100.0 g) to 50% hydrogen peroxide (400.0 g) so that the mixture was 40% hydrogen, peroxide and 20% triacetin, with the balance being water. The pH of the solution was 1.46 and the pH of a 1:100 dilution was 3.69. To accelerate storage characteristics, the sample was placed in an incubator set for 86-87° F. Table II shows the percent of hydrogen peroxide remaining and the percent of PAA generated over a period of more than six months.

TABLE II

| Days of Study | % Hydrogen Peroxide Remaining | % PAA Generated |
|---|---|---|
| 1 | 40.21 | 0.004 |
| 33 | 38.02 | 3.499 |
| 54 | 35.5 | 5.992 |
| 96 | 29.27 | 8.36 |
| 127 | 25.05 | 6.66 |
| 173 | 18.49 | 4.43 |
| 201 | 15.67 | 3.51 |

Table II indicates that after 96 days, the generation of PAA. maximized at 8.36% and corresponded to a loss of 10.94% hydrogen peroxide. Had all of the depleted hydrogen peroxide gone toward the generation of PAA, 24.45% PAA would have been generated. Because only 8.36% PAA was generated, unaccounted losses of hydrogen peroxide amounted to 7.2%.

Example 3

A formulation containing hydrogen peroxide and triacetin in a mole ratio of 5.8:1 was prepared by adding triacetin (37.5008 g) to 50% hydrogen peroxide 165.2504 g) so that the mixture was 31.75% hydrogen peroxide and 36.5% triacetin, with the balance being water. The pH of the solution was 1.57 and the pH of a 1:100 dilution was 5.17. To accelerate degradation, the sample was placed in an incubator set for 86-87° F. Table III shows the percent of hydrogen peroxide remaining and the percent of PAA generated over a period of six days.

TABLE III

| Days of Study | % Hydrogen Peroxide Remaining | % PAA Generated |
|---|---|---|
| 1 | 31.72 | 0.33 |
| 6 | 31.63 | 0.716 |

In this study, after six days, the mixture had lost only 0.09% hydrogen peroxide, yet had generated an additional 0.386% PAA. Had all the loss of hydrogen peroxide been due to the formation of PAA, only an additional 0.201% would have been generated. It is clear that the analytical methods employed for solutions that are high in hydrogen peroxide but low in PAA are subject to detection limit errors.

Example 4

A formulation containing hydrogen peroxide and triacetin in a mole ratio of 3.2:1 was prepared by adding triacetin (35.0 g) to 50% hydrogen peroxide (35.0 g) so that the mixture was 25% hydrogen peroxide and 50% triacetin, with the balance being water. The pH of the solution was 1.66 and the pH of a 1:100 dilution was 4.09. To accelerate degradation, the sample was placed in an incubator set for 86-87° F. Table IV shows the percent of hydrogen peroxide remaining and the percent of PAA generated over a period of 22 days.

TABLE IV

| Days of Study | % Hydrogen Peroxide Remaining | % PAA Generated |
|---|---|---|
| 1 | 25 | 0.62 |
| 8 | 24.51 | 1 |
| 15 | 24.17 | 1.17 |
| 22 | 23.68 | 1.14 |

Table IV indicates that after 15 days, the generation of PAA maximized at 1.17% and corresponded to a loss of 0.83% hydrogen, peroxide. Had all of the depleted hydrogen peroxide gone toward the generation of PAA, 1.86% PAA would have been generated. Because only 1.17% PAA was generated, unaccounted losses of hydrogen peroxide amounted to 0.31%.

Example 5

A formulation containing hydrogen, peroxide and triacetin in a mole ratio of 4.8:1. was prepared by adding triacetin. (37.50 g) to 50% hydrogen peroxide (56.25 g) so that the mixture was 30% hydrogen peroxide and 40% triacetin, with the balance being water. The pH of the solution was 1.67 and the pH of a 1:100 dilution was 4.62. To accelerate degradation, the sample was placed in an incubator set for 86-87° F. Table V shows the percent of hydrogen peroxide remaining and the percent of PAA generated over a period of 43 days.

TABLE V

| Days of Study | % Hydrogen Peroxide Remaining | % PAA Generated |
|---|---|---|
| 1 | 30.08 | 0.38 |
| 8 | 29.85 | 0.784 |
| 15 | 29.63 | 1.22 |
| 22 | 29.37 | 1.71 |
| 29 | 28.76 | 2.26 |
| 36 | 28.67 | 2.78 |
| 43 | 28.31 | 3.41 |

Table V shows that although there was a steady depletion in hydrogen peroxide, it was accompanied by the associative increase of PAA. At the end of the 43-day study, the composition had lost 1.77% hydrogen peroxide. Had all of the depleted hydrogen peroxide gone toward the generation of PAA, 3.96% PAA would have been generated. Because only 3.41% PAA was generated, unaccounted losses of hydrogen peroxide amounted to 0.24%.

Example 6

A formulation containing hydrogen peroxide and triacetin in a mole ratio of 6.42:1 was prepared by adding triacetin (25.0007 g) to 50% hydrogen peroxide (50.0007 g) so that the mixture was 33.33% hydrogen peroxide and 33.33% triacetin, with the balance being water. The pH of the solution was 1.56 and the pH of a 1:100 dilution was 5.15. To accelerate degradation, the sample was placed in an incubator set for 86-87° F. Table VI shows the percent of hydrogen peroxide remaining and the percent of PAA generated over a period of 36 days.

TABLE VI

| Days of Study | % Hydrogen Peroxide Remaining | % PAA Generated |
|---|---|---|
| 1 | 33.13 | 0.81 |
| 8 | 32.88 | 1.35 |
| 15 | 32.61 | 1.88 |
| 22 | 31.69 | 2.58 |
| 29 | 31.75 | 3.03 |
| 36 | 31.29 | 3.28 |

Table VI shows that although there was a steady depletion in hydrogen peroxide, it was accompanied by the associative increase of PAA. At the end of the 36-day study, the composition had lost 1.84% hydrogen peroxide. Had all of the depleted hydrogen peroxide gone toward the generation of PAA, 4.11 % PAA would have been generated. Because only 3.28% PAA was generated, unaccounted losses of hydrogen peroxide amounted to 0.37%.

Example 7

A 30-gallon batch of 50% hydrogen peroxide and triacetin was prepared by blending 137 lbs triacetin with 163 lbs 50% hydrogen peroxide so that the mixture was 27.15% hydrogen peroxide and 45.67% triacetin, with the balance being water. Thus, the mole ratio of hydrogen peroxide:triacetin was 3.8:1. The mixture was stored in an opaque drum, in a non-climate controlled environment. On storage, the mixture slowly formed PAA in the container. Since this reaction of hydrogen peroxide to PAA does not represent a destructive loss of total peroxygen, to determine the true stability of the hydrogen peroxide, both the hydrogen peroxide and the peracetic acid generated must be quantified and reported as total peroxygen recovered.

After 295 days of storage, the mixture was analyzed for total peroxygen recovered (expressed as hydrogen peroxide) to determine the percent loss of peroxygen. Using the ceric Sulfate-iodometric titration method, the PAA generated and the hydrogen peroxide remaining were measured. The total peroxygen recovered after 295 days and the theoretical initial concentrations are shown in Table VII. All peroxygen is expressed as % hydrogen peroxide.

TABLE VII

|  | Initial Theoretical % | % (after 295 days) |
| --- | --- | --- |
| Hydrogen Peroxide Recovered | 27.17 | 15.20 |
| PAA formed | 0 | 15.57 |
| Hydrogen Peroxide Reacted to form PAA | 0 | 6.97 |
| Total Recovered Hydrogen Peroxide | 27.17 | 22.17 |
| Total Hydrogen Peroxide Unproductive Loss |  | 5.00 |

After 295 days, 22.17% of the total peroxygen was recovered as either titratable hydrogen peroxide or hydrogen peroxide reacted to form PAA. To determine the stability of the peroxygen in the mixture, the total recovered hydrogen, peroxide after 295 days (22.17%) was subtracted from the total recovered hydrogen peroxide of the initial theoretical value (27.17%). The result, 5%, is the loss of peroxygen (expressed as hydrogen peroxide) after 295 days of storage in a non-climate controlled environment.

4. Methods of Generating Non-Equilibrium PAA on Site at the Point-of-Use

Methods of continuously or intermittently generating non-equilibrium solutions of PAA on a site having a point-of-use of PAA for use as a disinfectant or sanitizer, using a source of water that is an aqueous stream or by a batch process using water in a container, are provided.

In one embodiment, a method of continuously or intermittently generating non-equilibrium solutions of PAA on a site having a point-of-use, using a source of water that is an aqueous stream, comprises the following steps.

(a) Providing water.

Flowing water is provided on a site having a point-of-use of peracetic acid.

The water may be flowing in, for example, a pipe, a flume, a canal, or other types of aqueous streams. The water pressure should be regulated and the flow rate should be monitored or measured. Any suitable flow meter may be used, such as a rotameter, a magnetic flow meter, an ultrasonic flow meter, a Doppler flow meter, a differential-pressure flow meter, a turbine flow meter, or a Coriolis flow meter.

The water should be softened, deionized, or of sufficient low hardness that it will not precipitate calcium salts when the alkali metal or earth alkali metal hydroxide is introduced in step (d).

(b) Introducing a hydrogen peroxide-acetyl precursor solution to the water.

A hydrogen peroxide-acetyl precursor solution is provided on the site having the point-of-use of the PAA. The hydrogen peroxide-acetyl precursor solution may be prepared by the steps set forth in section 3 above. The hydrogen peroxide-acetyl precursor solution may be prepared off site and then transported to the site having the point-of-use, or the acetyl precursor and the aqueous hydrogen peroxide may be transported to the site having the point-of-use and used to prepare the hydrogen peroxide-acetyl precursor solution on the site.

A preferable liquid acetyl precursor is triacetin. When triacetin is used, a hydrogen peroxide-triacetin solution is introduced.

The hydrogen peroxide-acetyl precursor solution is introduced to the flowing water in an amount such that the hydrogen peroxide-acetyl precursor solution is about 5.6% to about 22.5% of the total.

The hydrogen peroxide-acetyl precursor solution is pumped from its container into the aqueous water stream, for example, through an injection quill mounted on the pipe. Any suitable pump capable of overcoming the pressure of the water flowing in the pipe may be used. Examples include a solenoid-driven or air-driven diaphragm pump or a peristaltic pump. The rate at which the hydrogen peroxide-acetyl precursor solution is pumped into the flowing water is governed by a controller that is interfaced to a flow meter that is measuring the flow of the water. In this way, the rate at which the hydrogen peroxide-acetyl precursor solution is pumped may be matched to the flow of the water in the aqueous stream. If the flow of the water slows, the rate at which the hydrogen peroxide-acetyl precursor solution is pumped should slow accordingly. If the flow of the water stops, the hydrogen peroxide-acetyl precursor pump should stop.

As an alternative to step (b), the liquid acetyl precursor and the solution of aqueous hydrogen peroxide may be introduced to the water separately, either simultaneously or sequentially. If they are introduced sequentially, either one may be added first. If the liquid acetyl precursor and the aqueous hydrogen peroxide are introduced separately, rather than as an hydrogen peroxide-acetyl precursor solution, then in step (c) the liquid acetyl precursor and the aqueous hydrogen peroxide are mixed with the water to form a mixture.

(c) Mixing the hydrogen peroxide-acetyl precursor solution and the water to form a mixture.

Any mixing device suitable for mixing liquids may be used. An example is a static mixer located just after the point that the hydrogen peroxide-acetyl precursor solution is introduced to the flowing water. One type of static mixer utilizes a non-moving element such as a series of baffles. As the mixture flows through the static mixer under the motive force of the flowing water, the non-moving element divides the flow several times to provide radial mixing. Another type of static mixer utilizes a series of obstructions, such as column packing or glass beads, provided there is a low differential pressure drop across the mixer. The obstructions provide for turbulent mixing of the hydrogen peroxide-acetyl precursor solution and the flowing water. The mixing should yield a homogeneous solution with no concentration gradients before the next step is performed. The velocity of the water will determine the time it takes to complete the mixing and the efficiency of the mixing. For example, with ¾" pipe, a static mixer of ¾" diameter and 6" long, and a velocity of about 1 gal/mm., mixing should be accomplished in less than about one second.

(d) Adding an aqueous source of an alkali metal or earth alkali metal hydroxide to the mixture.

An aqueous source of an alkali metal or earth alkali metal hydroxide is provided on the site having the point-of use. A preferable aqueous source of an alkali metal hydroxide is sodium hydroxide, and 50% sodium hydroxide is most preferable. Other suitable alkali metal hydroxides include 45% potassium hydroxide.

Sufficient 50% NaOH is added to the flowing mixture such that the amount of sodium hydroxide is about 1.82% to about 7.28% of the total amount. When the acetyl precursor is triacetin, a preferred mole ratio of NaOH:hydrogen peroxide:triacetin is about 4.2:3.8:1.

The 50% NaOH solution is added to the mixture by pumping it from its container with a suitable pumping device and into the mixture through an injection quill mounted on the pipe. Any suitable pump capable of overcoming the hydraulic pressure of the pipe may be used. Examples include a solenoid-driven or air-driven diaphragm pump or a peristaltic pump.

The rate at which the 50% NaOH solution, is pumped into the pipe is governed by the same controller that is interfaced to both the flow meter that is measuring the flow of the mixture and the pump controlling the rate of introduction of the hydrogen peroxide-acetyl precursor solution. In this way, the rate at which the 50% NaOH solution is introduced may be matched to both the flow of the mixture and the rate of introducing the hydrogen peroxide-acetyl precursor solution. If the flow of the mixture slows for any reason, the rate at which the 50% NaOH solution is pumped should slow accordingly. If the flow of the mixture stops, the 50% NaOH pump should stop as well.

Step (d) may be performed after step (e), or it may be performed simultaneously with step (b).

(e) Forming a reaction medium comprising a non-equilibrium solution of peracetic acid.

The reaction median that is formed in this step almost instantaneously forms a non-equilibrium solution of PAA. The hydrogen peroxide reacts with the acetyl precursor to form peracetic acid. Depending upon the temperature of the water, the efficiency of mixing, and the mole ratio of NaOH:hydrogen peroxide:acetyl precursor employed, the amount of hydrogen peroxide and acetyl precursor that are converted into PAA is maximized within about 30 seconds to about five minutes.

The non-equilibrium, solutions of PAA prepared by this method comprise PAA, unreacted hydrogen peroxide, unreacted acetyl precursor, the product of the perhydrolysis reaction of the acetyl precursor, the aqueous source of alkali metal or earth alkali metal hydroxide, and water. When the acetyl precursors is triacetin, the product of the perhydrolysis reaction is 1, 2, 3-propanetriol (glycerine).

This method may also include an optional step after step (e) of sampling the reaction medium at various times after the addition of the aqueous source of alkali metal or earth alkali metal hydroxide to determine the time required under the existing conditions to maximize the amount of hydrogen peroxide and acetyl precursor that are converted into PAA. This may be accomplished by directing the flow of the reaction medium through a series of residence chambers equipped with sampling ports. The residence chambers are designed to be of sufficient volume such that a certain amount of time has elapsed since the introduction of the 50% NaOH. Thus, at any given flow rate in the pipe, the first residence chamber is of a volume such that 30 seconds have elapsed since the introduction of 50% NaOH, one minute has elapsed by the time the flow reaches the sampling port immediately after the second residence chamber, and additional time elapses by the time the flow reaches the remaining sampling ports. Up to four residence chambers and sampling ports may be placed in series such as this to provide the user with about 30 seconds to five minutes of residence time after tire introduction of the 50% NaOH. Once the flow of the reaction medium has been established, samples are drawn from all four sampling ports associated with the residence chambers and analyzed for peracetic acid. The sample which registers the highest amount of peracetic acid is deemed to be drawn from the sampling port associated with the residence chamber corresponding to the time of maximum conversion of the acetyl precursor into peracetic acid. At this point, the entire flow of reaction medium is directed through the sampling point of maximum conversion of acetyl precursor and to the point-of-use.

In another embodiment, a method of continuously or intermittently generating a Non-equilibrium solution of PAA on a site having a the point-of-use in a batch process comprises the following steps:

(a) Providing water.

A container of water, such as a mixing tank or other vessel, is provided on a site having a point-of-use of peracetic acid. The water should be softened, deionized, or of sufficient low hardness that it will not precipitate calcium salts when the alkali metal or earth alkali metal hydroxide is introduced in step (d).

(b) Introducing a hydrogen peroxide-acetyl precursor solution to the water.

A hydrogen peroxide-acetyl precursor solution is provided on the site having the point-of-use of the PAA. The hydrogen peroxide-acetyl precursor solution may be prepared by the steps set forth in section 3 above. The hydrogen peroxide-acetyl precursor solution may be prepared off site and then transported to the site having the point-of-use, or the acetyl precursor and the aqueous hydrogen peroxide may be transported to the site having the point-of-use and used to prepare the hydrogen peroxide-acetyl precursor solution on the site.

A preferable liquid acetyl precursor is triacetin. When triacetin is used, a hydrogen peroxide-triacetin solution is introduced.

The hydrogen peroxide-acetyl precursor solution is introduced to the water in an amount such that the hydrogen peroxide-acetyl precursor solution is about 5.6% to about 22.5% of the total.

The hydrogen peroxide-acetyl precursor solution is pumped from its container into the container of water through an injection quill mounted on the side of the container of water. Any suitable pump may be used. Examples include a solenoid-driven or air-driven diaphragm pump or a peristaltic pump.

As an alternative to step (b), the liquid acetyl precursor and the solution of aqueous hydrogen peroxide may be introduced to the water separately, either simultaneously or sequentially. If they are introduced sequentially, either one may be added first. If the liquid acetyl precursor and the aqueous hydrogen peroxide are introduced separately, rather than as an hydrogen peroxide-acetyl precursor solution, then in step (c) the liquid acetyl precursor and the aqueous hydrogen peroxide are mixed with the water to form a mixture.

(c) Mixing the hydrogen peroxide-acetyl precursor solution and the water to form a mixture.

Any mixing device suitable tor mixing liquids may be used. An example is an overhead stirrer, such as an agitator blade. The container of water is equipped with a baffle to assist the process of mixing. The mixing should yield a homogeneous solution with no concentration gradients before the next step is performed.

(d) Adding an aqueous source of an alkali metal or earth, alkali metal hydroxide to the mixture.

An aqueous source of an alkali metal or earth alkali metal hydroxide is provided on the site having the point-of-use. A preferable aqueous source of an alkali metal hydroxide is sodium hydroxide, and 50% sodium hydroxide is most preferable. Other suitable alkali metal hydroxides include 45% potassium hydroxide.

Sufficient 50% NaOH is added to the mixture such that the amount of sodium hydroxide is about 1.82% to about 7.28% of the total amount. When the acetyl precursor is triacetin, a preferred mole ratio of NaOH:hydrogen peroxide:triacetin is about 4.2:3.8:1.

The 50% NaOH solution is added to the mixture by pumping it from its container with a suitable pumping device and into the mixture through an injection quill mounted on the side of the container of water. Any suitable pump may be used. Examples include a solenoid-driven or air-driven diaphragm pump or a peristaltic pump.

Step (d) may be performed after step (c), or it may be performed simultaneously with step (b).

(e) Forming a reaction medium comprising a non-equilibrium solution of peracetic acid.

The reaction medium that is formed in this step almost instantaneously forms a non-equilibrium solution of PAA. The hydrogen peroxide reacts with the acetyl precursor to form peracetic acid. Depending upon the temperature of the water, the efficiency of mixing, and the mole ratio of NaOH: hydrogen peroxide:acetyl precursor employed, the amount of hydrogen peroxide and acetyl precursor that are converted into PAA is maximized within about 30 seconds to about five minutes.

The non-equilibrium solutions of PAA prepared by this method comprise PAA, unreacted hydrogen peroxide, unreacted acetyl precursor, the product of the perhydrolysis reaction of the acetyl precursor, the aqueous source of alkali metal or earth alkali metal hydroxide, and water. When the acetyl precursors is triacetin, the product of the perhydrolysis reaction is 1, 2, 3-propanetriol (glycerine).

While not wishing to be bound by theory, it is believed that under elevated pH conditions created by the addition of a source of alkali metal hydroxide or earth alkali metal hydroxide, hydrogen peroxide dissociates according to the following equation:

$$H_2O_2 = H^+ + HO_2^-$$

The perhydroxyl anion ($HO_2^-$) then affects nucleophilic substitution reactions on the carbonyl groups of the acetyl precursor in a perhydrolysis reaction to form peracetic acid and the product of the perhydroloysis reaction of the acetyl precursor. When the acetyl precursor is triacetin and all three acetyl groups are reacted, then the product of the perhydrolysis reaction is 1, 2, 3-propanetriol (glycerine).

In these methods, the perhydrolysis reaction is rapid and the maximum amount of PAA is generated within about 30 seconds to about five minutes at ambient temperature. The methods efficiently utilize the acetyl precursor and the source of hydrogen peroxide. When triacetin is used, assuming all three acetyl groups are reacted, about 40.9% to about 85.7% of the triacetin is converted into PAA. The percent of hydrogen peroxide remaining is about 0.078% to about 1.88%.

The non-equilibrium solutions of PAA prepared by these methods have several unique characteristics. The PAA solutions have high levels of PAA, from about 1% to about 7.1%. In addition, the PAA solutions are alkaline, having a pH of about 11.2 to about 13.37.

The non-equilibrium solutions of PAA may be immediately introduced to the receiving water at the point-of-use. Alternatively, the solutions may be stabilized by halting the decomposition of the PAA by adding a source of acid to lower the elevated pH of the reaction medium caused by the addition of an alkali metal or earth alkali metal, hydroxide, and to provide neutral to mildly acid pH conditions to stabilize the PAA to elevated pH degradation. The acid-stabilized PAA solutions can then be stored and used at the point-of-use as required throughout a working day.

The non-equilibrium PAA solutions produced by these methods can be advantageously used wherever traditional equilibrium solutions of PAA are used. Thus, the PAA solutions may be used as a disinfectant and sanitizer in the dairy, food, and beverage processing industries for clean-in-place pipeline and equipment cleaning; for fruit and vegetable washing; and in the treatment of meat, poultry, and seafood products. These PAA solutions may also be used in the treatment of cooling water, oil and gas process water, and municipal wastewater. Other uses include slime and biofilm removal in papermaking processes.

For both of the above methods, steps (a) through (e) may be performed on a continuous or intermittent basis. In a continuous basis, the steps are performed under conditions of steady state, and the PAA solution is produced at the same rate as a function of time. However, intermittent performing of steps (a) through (e) is possible if the demand for the PAA solution drops for any reason (e.g., change in working shift or the target level of PAA in the receiving water has been achieved), in which case, steps (a) through (e) may be discontinued and resumed when the demand increases.

Example 8

Tests were performed using about one liter of reverse osmosis (RO) or softened water which was buffered to an alkaline pH. The buffering media, included 0.1 and 0.2 M $Na_2CO_3$ solutions, in addition to 0.1 and 0.2 M NaOH solutions. Sufficient buffering media was added to the water in order to achieve the desired pH. The amount of hydrogen peroxide (introduced as 50% hydrogen peroxide) and triacetin used in the tests is summarized in Table VIII. The reactants were introduced to the solution in one of three ways: simultaneously (referred to in Table VIII as "double"), sequentially (triacetin followed shortly by hydrogen peroxide), or by mixing the hydrogen peroxide and triacetin together and adding them in a single charge (referred to in Table VIII as "mixed"). All testing was performed at ambient temperature as the one-liter beaker was stirred with a magnetic stir bar. Using the ceric sulfate-iodometric titration method, the percent of PAA generated and the percent of hydrogen peroxide remaining were measured five minutes after introduction of the reactants to the buffer. The percent of the triacetin acetyl donor converted to PAA was calculated, assuming all three acetyl groups were available for perhydrolysis.

TABLE VIII

| Test # | Moles Hydrogen Peroxide/ Mole Triacetin | Type of Addition (Double Sequential or Mixed) | pH of Buffer | Hydrogen Peroxide Used (Wt., g) | Triacetin Used (Wt., g) | % PAA Generated | % Hydrogen Peroxide Remaining | % Triacetin Converted to PAA |
|---|---|---|---|---|---|---|---|---|
| 1 | 4.99 | Double | 10.50 | 8.60 | 5.53 | 0.170 | 0.329 | 29.6% |
| 2 | 5.47 | Double | 10.50 | 8.60 | 5.04 | 0.178 | 0.333 | 33.9% |
| 3 | 5.45 | Double | 10.80 | 8.61 | 5.07 | 0.192 | 0.329 | 36.4% |

TABLE VIII-continued

| Test # | Moles Hydrogen Peroxide/ Mole Triacetin | Type of Addition (Double Sequential or Mixed) | pH of Buffer | Hydrogen Peroxide Used (Wt., g) | Triacetin Used (Wt., g) | % PAA Generated | % Hydrogen Peroxide Remaining | % Triacetin Converted to PAA |
|---|---|---|---|---|---|---|---|---|
| 4 | 5.68 | Double | 11.00 | 8.87 | 5.01 | 0.201 | 0.322 | 38.6% |
| 5 | 5.72 | Double | 11.00 | 9.13 | 5.12 | 0.068 | 0.416 | 12.8% |
| 6 | 5.49 | Double | 12.42 | 8.60 | 5.02 | 0.169 | 0.306 | 32.4% |
| 7 | 5.59 | Double | 12.91 | 8.60 | 4.93 | 0.320 | 0.265 | 62.4% |
| 8 | 5.53 | Double | 12.80 | 8.69 | 5.04 | 0.335 | 0.273 | 63.9% |
| 9 | 25.0 | Double | 12.65 | 9.03 | 1.16 | 0.104 | 0.413 | 85.9% |
| 10 | 5.26 | Double | 12.60 | 8.70 | 5.30 | 0.298 | 0.247 | 54.1% |
| 11 | 5.52 | Sequential | 12.83 | 8.68 | 5.04 | 0.276 | 0.248 | 52.4% |
| 12 | 5.47 | Sequential | 12.81 | 17.11 | 10.03 | 0.120 | 0.371 | 11.4% |
| 13 | 28.8 | Mixed | 11.12 | 8.74 | 0.973 | 0.039 | 0.398 | 38.9% |
| 14 | 28.8 | Mixed | 11.99 | 8.75 | 0.974 | 0.038 | 0.374 | 37.9% |
| 15 | 28.8 | Mixed | 13.02 | 8.69 | 0.967 | 0.055 | 0.367 | 55.2% |
| 16 | 28.8 | Mixed | 7.91 | 8.70 | 0.968 | 0.024 | 0.435 | 23.7% |
| 17 | 28.8 | Mixed | 11.22 | 8.76 | 0.975 | 0.029 | 0.309 | 28.4% |
| 18 | 28.8 | Mixed | 12.07 | 8.68 | 0.966 | 0.028 | 0.311 | 27.7% |
| 19 | 28.8 | Mixed | 13.22 | 8.72 | 0.971 | 0.026 | 0.321 | 25.6% |
| 19 dup | 25.2 | Mixed | 12.97 | 8.77 | 1.12 | 0.031 | 0.249 | 26.5% |
| 20 | 25.2 | Mixed | 12.98 | 9.08 | 1.16 | 0.066 | 0.393 | 54.5% |
| 20 dup | 25.5 | Mixed | 13.00 | 9.10 | 1.16 | 0.074 | 0.409 | 61.0% |
| 21 | 25.2 | Mixed | 13.02 | 9.10 | 1.16 | 0.02 | 0.261 | 16.5% |
| 21 dup | 25.2 | Mixed | 12.99 | 9.12 | 1.16 | 0.017 | 0.376 | 14.0% |
| 22 | 16.0 | Mixed | 12.99 | 5.80 | 1.16 | 0.070 | 0.246 | 57.7% |
| 23 | 16.0 | Mixed | 13.05 | 5.79 | 1.16 | 0.013 | 0.189 | 10.7% |
| 24 | 16.0 | Mixed | 12.55 | 5.78 | 1.16 | 0.031 | 0.234 | 25.6% |
| 25 | 16.0 | Mixed | 12.49 | 5.80 | 1.16 | 0.013 | 0.144 | 10.7% |
| 26 | 16.0 | Mixed | 12.01 | 5.85 | 1.17 | 0.016 | 0.259 | 13.1% |
| 27 | 16.0 | Mixed | 12.05 | 5.82 | 1.16 | 0.011 | 0.080 | 9.0% |
| 28 | 16.0 | Mixed | 10.50 | 0.601 | 0.120 | 0.00077 | 0.028 | 6.1% |
| 29 | 16.0 | Mixed | 10.97 | 0.595 | 0.119 | 0.00023 | 0.021 | 1.8% |
| 30 | 16.0 | Mixed | 10.50 | 0.614 | 0.123 | 0.00012 | 0.019 | 0.9% |
| 31 | 16.0 | Mixed | 10.97 | 0.595 | 0.119 | 0.00035 | 0.018 | 2.8% |

Table VIII shows that the amount of PAA generated was independent of the method of introducing the triacetin and hydrogen peroxide to the buffer solutions. It can be seen that the pH of the buffer had a significant effect on the percent of the triacetin that was converted into PAA. Only when the pH was above 12 was a meaningful percent of the triacetin converted into PAA.

Example 9

A mixture of triacetin and hydrogen peroxide was prepared by blending 50% hydrogen peroxide (63.4%) and triacetin (36.0%). Thus, the mole ratio of hydrogen peroxide:triacetin was 5.57:1. The mixture (13.68 g) was added to soft water such that the final solution contained 5 g/L of triacetin and had a pH of 4.1. Then, in successive experiments, sufficient 50% NaOH was added to the beaker so that the mole ratio of NaOH:TA was varied from 3:1 (obtained by introducing 5.40 g of 50% NaOH) to 8:1 (obtained by introducing 14.68 g of 50% NaOH). Using the ceric sulfate-iodometric titration method, the percent of PAA generated and the percent of hydrogen peroxide remaining were measured over the next 20 minutes. The method was performed in duplicate for each sample point. The averages of the results for the 6:1 mole ratio of NaOH:TA are shown in Table IX.

TABLE IX

| Time (min) | % PAA Generated | % Hydrogen Peroxide Remaining | % Triacetin Converted to PAA (3 acetyls) |
|---|---|---|---|
| 0 | 0.015 | 0.437 | 2.9 |
| 1 | 0.275 | 0.298 | 53.1 |
| 3 | 0.312 | 0.274 | 60.2 |
| 5 | 0.326 | 0.258 | 62.9 |
| 11 | 0.302 | 0.233 | 58.3 |
| 21 | 0.246 | 0.199 | 47.5 |

It can be seen that even before the introduction of 50% NaOH, some PAA was present in solution as a result of being generated in the diluted mixture of the two components. Upon addition of the NaOH, PAA was immediately generated, with the maximum amount of 0.326% occurring at five minutes, corresponding to a yield of 62.9% assuming all three acetyl groups of triacetin were available for perhydrolysis.

This exercise was repeated for mole ratios of NaOH:triacetin ranging from 3:1 to 8:1. Table X summarizes the next set of data and shows the maximum percent of PAA generated, the time after the addition of NaOH that it took to reach the maximum percent of PAA generated, the pH after the addition of the NaOH, the percent of hydrogen peroxide remaining at the time of the maximum percent of PAA, and the calculated percent of triacetin converted to PAA assuming that all three acetyl groups were available for perhydrolysis.

TABLE X

| Mole ratio NaOH:TA | Time at Max. PAA (min) | Max % PAA Generated | % Hydrogen Peroxide Remaining | % Triacetin Converted to PAA (3 acetyls) | pH |
|---|---|---|---|---|---|
| 3:1 | 3 | 0.229 | 0.291 | 43.8 | 11.2 |
| 4:1 | 6 | 0.285 | 0.251 | 54.8 | 11.3 |
| 6:1 | 5 | 0.326 | 0.258 | 62.9 | 11.6 |
| 8:1 | 3 | 0.335 | 0.271 | 64.7 | 12.2 |

It can be seen that the amount of PAA generated, and hence the conversion of triacetin into PAA, increased with the increasing mole ratio of NaOH:TA. For all four mole ratios employed, the maximum amount of PAA was generated between three and six minutes. The optimum mole ratio of NaOH:TA was 6:1 as it resulted in an efficient utilization of triacetin converted into PAA, and because the pH of the resulting reaction medium would have less impact on the pH of the receiving water than the higher pH of the reaction medium resulting from the 8:1 mole ratio.

Example 10

A series of experiments was then performed in which the mole ratio of NaOH:TA was fixed at 8:1 and the mole ratio of hydrogen peroxide-triacetin was varied from 2:1 to 8:1. Triacetin (5 g) was added to about 965 mL of softened water along with 50.7% hydrogen peroxide in successive tests (3.06 g for the 2:1 mole ratio; 6.19 g for the 4:1 mole ratio; 9.23 g tor the 6:1 mole ratio; and 12.32 g for the 8:1 mole ratio) to yield a solution with a pH of about 4.8-5.5. The volume of the mixture was adjusted to 990 mL with softened water. With mixing, 50% NaOH (14.67 g) was introduced. Using the ceric sulfate-iodometric titration method, the percent of PAA generated and the percent of hydrogen peroxide remaining were measured over the next 20 minutes. The method was performed in duplicate for each sample point The averages of the results for the kinetic run employing the mole ratio of 8:6:1 NaOH:hydrogen peroxide:TA are shown in Table XI.

TABLE XI

| Time (min) | % PAA Generated | % Hydrogen Peroxide Remaining | % Triacetin Converted to PAA (3 acetyls) |
|---|---|---|---|
| 1 | 0.331 | 0.317 | 63.8 |
| 3 | 0.330 | 0.303 | 63.6 |
| 5 | 0.319 | 0.303 | 61.5 |
| 10 | 0.300 | 0.295 | 57.8 |
| 20 | 0.256 | 0.274 | 49.3 |

Upon addition, of the NaOH, PAA was immediately generated, with the maximum amount of 0.331% occurring after just one minute, corresponding to a calculated conversion of triacetin into PAA of 63.8%, assuming that all three acetyl groups of triacetin were available for perhydrolysis.

This exercise was repeated for mole ratios of hydrogen peroxide:triacetin ranging from 2:1 to 6:1. Table XII summarizes the data and shows the maximum percent of PAA generated, the time after the addition of NaOH that it took to reach the maximum percent of PAA generated, the pH after the addition of the NaOH, the percent of hydrogen peroxide remaining at the time of the maximum percent of PAA, and the calculated percent of triacetin converted to PAA assuming that all three acetyl groups were available for perhydrolysis.

TABLE XII

| Mole Ratio Hydrogen Peroxide: Triacetin | Time at Max. PAA (min) | Max % PAA Generated | % Hydrogen Peroxide Remaining | % Triacetin Converted to PAA (3 acetyls) | pH |
|---|---|---|---|---|---|
| 2:1 | 3 | 0.214 | 0.079 | 40.9 | 12.6 |
| 4:1 | 1 | 0.272 | 0.195 | 51.9 | 12.4 |
| 6:1 | 1 | 0.331 | 0.317 | 63.8 | 12.3 |
| 8:1 | 3 | 0.374 | 0.445 | 72.0 | 11.9 |

It can be seen that the amount of PAA generated, and hence the conversion of triacetin into PAA. Increased with the increasing mole ratio of hydrogen peroxide:triacetin. For all four mole ratios employed, the maximum amount of PAA was generated between one and three minutes. The optimum mole ratio of hydrogen peroxide:triacetin was 8:1 as it resulted in the most efficient utilization of triacetin converted into PAA.

Example 11

A further series of experiments was performed in which the mole ratio of hydrogen peroxide to triacetin was fixed at 4:1 and the molar ratio of NaOH to triacetin was varied from 3:1 to 8:1. Triacetin (5 g) was added to around 975 mL of softened water along with 50.7% hydrogen peroxide (6.18 g) to yield a solution with a pH of 4.8 to 5.3. With mixing, 50% NaOH was introduced in successive tests (5.51 g for the 3:1 mole ratio; 7.30 g for the 4:1 mole ratio; 11.03 g for the 6:1 mole ratio; and 14.67 g for the 8:1 mole ratio). The volume of the mixture was adjusted to 1000 mL with softened water. Using the ceric sulfate-iodometric titration method, the percent of PAA generated and the percent of hydrogen peroxide remaining were measured over the next 20 minutes. The method was performed in duplicate for each sample point. The averages of the results for the kinetic run employing the mole ratio of NaOH:hydrogen peroxide:triacetin of 4:4:1 are shown in Table XIII.

TABLE XIII

| Time (min) | % PAA Generated | % Hydrogen Peroxide Remaining | % Triacetin Converted to PAA (3 acetyls) |
|---|---|---|---|
| 1 | 0.247 | 0.207 | 47.3 |
| 3 | 0.280 | 0.178 | 53.6 |
| 5 | 0.292 | 0.167 | 55.9 |
| 10 | 0.267 | 0.142 | 51.1 |
| 20 | 0.229 | 0.111 | 43.8 |

Upon addition of the NaOH, PAA was immediately generated, with the maximum amount of 0.292% occurring after five minutes, corresponding, to a calculated conversion of 55.9% triacetin into PAA assuming that all three acetyl groups of triacetin were available for perhydrolysis.

This exercise was repeated tor mole ratios of NaOH:TA ranging from 3:1 to 8:1. Table XIV summarizes the data and records the maximum percent of PAA generated, the time after the addition of NaOH that it took to reach the maximum percent of PAA generated, the pH after the addition of the NaOH, the percent of hydrogen peroxide remaining at the time of the maximum percent of PAA, and the calculated percent of triacetin converted to PAA assuming that all three acetyl groups were available for perhydrolysis.

TABLE XIV

| Mole Ratio NaOH:TA | Time at Max. PAA (min) | Max % PAA Generated | % Hydrogen Peroxide Remaining | % Triacetin Converted to PAA (3 acetyls) | pH |
|---|---|---|---|---|---|
| 3:1 | 3 | 0.246 | 0.202 | 47.2 | 11.3 |
| 4:1 | 5 | 0.292 | 0.167 | 55.9 | 11.6 |
| 6:1 | 3 | 0.290 | 0.181 | 55.6 | 12.2 |
| 8:1 | 3 | 0.272 | 0.195 | 51.9 | 12.4 |

It can be seen that the amount of PAA generated maximized when the mole ratio of NaOH:hydrogen peroxide:triacetin was 4:4:1. The optimum mole ratio of NaOH:hydrogen peroxide:triacetin was 4:4:1 as it resulted in an efficient utilization of triacetin converted into PAA, and because the pH of the resulting reaction medium would have less impact on the pH of the receiving water than the higher pH of the reaction medium resulting from the 4:6:1 mole ratio of NaOH:hydrogen peroxide:triacetin. For all four mole ratios employed, the maximum amount of PAA was generated between three and five minutes.

Example 12

In the first test, a mixture of triacetin and hydrogen peroxide was prepared by blending 50% hydrogen peroxide (54, 24%) and triacetin (45.76%), Thus, the mole ratio of hydrogen peroxide:triacetin was 3.65:1. The mixture (51.22 g) was dissolved in soft water (911.9 g) in a one-liter beaker to yield a solution with a pH of 6.47. Then, 50% NaOH (36.47 g) was introduced with stirring. Thus, the mole ratio of the combined mixture of NaOH:hydrogen peroxide:triacetin was 4.2:3.8:1. The pH of the resulting solution initially measured 12.1. Using the ceric sulfate-iodometric titration method, the PAA generated and the hydrogen peroxide remaining were measured over the next 10 minutes. It was noticed that the sample temperature rose immediately upon addition of the 50% NaOH.

In the second test, the first test was repeated except that the water was chilled soft water.

In the third test, the first test was repeated using three times the original amount of hydrogen peroxide:triacetin mixture and three times the original amount of 50% NaOH. The mole ratio of the combined mixture of NaOH:hydrogen peroxide:triacetin remained the same as before, at 4.2:3.8:1. The hydrogen peroxide and triacetin mixture (153.96 g) was introduced to chilled soft water (735.6 g) in a one-liter beaker to yield a solution with an initial pH of 5.14. Then, 50% NaOH (111.21 g) was introduced. Using the ceric sulfate-iodometric titration method, the PAA generated and the hydrogen peroxide remaining were measured over the next 10 minutes.

In the fourth test, the first test was repeated using four times the original amount of hydrogen peroxide:triacetin mixture and four times the original amount of 50% NaOH. The mole ratio of the combined mixture of NaOH:hydrogen peroxide:triacetin remained the same as before, at 4.2:3.8:1. The hydrogen peroxide and triacetin mixture (204.7 g) was introduced to chilled soft water (647.5 g) in a one-liter beaker to yield a solution with an initial pH of 6.32. Then, 50% NaOH (155.4 g) was introduced. Using the ceric sulfate-iodometric titration method, the PAA generated and the hydrogen peroxide remaining were measured over the next 10 minutes.

Table XV summarizes the results obtained for the four tests and shows the initial and final solution temperatures, the pH of the solution after the addition of the 50% NaOH, the maximum percent of PAA generated, the time of maximum PAA generation, and the percent of hydrogen peroxide remaining.

TABLE XV

| Test # | Initial Temp. (° F.) | Final Temp. (° F.) | Final pH | Max. % PAA Generated (time, min) | % Hydrogen Peroxide Remaining |
|---|---|---|---|---|---|
| 1 | NM | NM | 12.14 | 1.71 (1) | 0.58 |
| 2 | 38 | 50 | 12.67 | 2.1 (4) | 0.43 |
| 3 | 44 | 88 | 12.77 | 6.3 (1) | 1.18 |
| 4 | 34 | 92 | 13.17 | 7.2 (1) | 1.88 |

NM = not measured

Table XVI shows the percent of hydrogen peroxide convened overall, the percent of hydrogen peroxide converted to PAA, and the percent of triacetin converted to PAA (assuming that all three acetyl groups on triacetin are available tor conversion to PAA) for each of the tests in Table XV.

TABLE XVI

| Test # | % Hydrogen Peroxide Converted Overall | % Hydrogen Peroxide Converted to PAA (at maximum conversion time) | % Triacetin Converted to PAA (3 acetyls) |
|---|---|---|---|
| 1 | 67.8 | 88.1 | 69.7 |
| 2 | 68.8 | 94.4 | 85.8 |
| 3 | 71.6 | 94.3 | 85.7 |
| 4 | 66.1 | 88.1 | 73.8 |

The data in Tables XV and XVI indicate that far higher amounts of PAA are possible if the 50% sodium hydroxide solution is the last component of the mixture to be introduced. Further, up to 7.1% PAA was generated, although this solution got hot despite chilling the source water. Generation of the 6.3% PAA solution was very efficient because it represented a high 85.7% utilization of triacetin converted into PAA. There was clearly a linear relationship between Test 2, which generated 2.1% PAA, and Test 3, which utilized three times more of the reactants and generated 6.3% PAA, The data in Table XV indicate that the time of maximum conversion of triacetin was between one and four minutes. Thereafter, the amount of PAA in solution is reduced because it undergoes high pH degradation slowly over the following 10 minutes.

Example 13

FIG. 1 is a schematic representation of an example of a system 10 that was used to perform an embodiment of one of the methods described above to prepare a non-equilibrium solution of PAA on a site having a point-of-use. Triacetin was used as the acetyl precursor and 50% sodium hydroxide was used as the aqueous source of an alkali metal hydroxide.

A container 120 of a hydrogen peroxide-acetyl precursor solution, which was a hydrogen peroxide-triacetin solution, and a container 140 of 50% sodium hydroxide were each equipped with chemical delivery diaphragm pumps 115 and 135, respectively. Inlet water 90, which was softened, was provided from a water source on the site having the point-of-use. Inlet water 90 was directed through a pressure regulator 100 and flow meter 105, then into a section of pipe where the hydrogen peroxide-triacetin solution was introduced through injection quill 110. Mixing was accomplished using static mixer 125. Then, the sodium hydroxide solution was added through injection quill 130 to form a reaction medium.

The hydrogen peroxide-triacetin solution and the sodium hydroxide solution may be added in a sequential manner as described, where the hydrogen peroxide-triacetin solution was added first, or they may be added to the water simultaneously through a "T" fitting placed before static mixer 125. If a T fitting is used, the hydrogen peroxide-triacetin solution and the 50% sodium hydroxide solution are introduced to opposite ends of the T fitting and the mixture is injected into the pipe of water. In other embodiments, the hydrogen peroxide and triacetin may be added separately, or sequentially, with either one first, or simultaneously, with the sodium hydroxide added either simultaneously with, or after, the hydrogen peroxide and triacetin.

The reaction medium was introduced to a residence chamber 145 which provided reaction time and contained a packing material to promote mixing. Residence chamber 145 was designed to be of a volume such that at a total flow rate of one gallon per minute, by the time the reaction medium reached sampling port 160, 30 seconds had elapsed since the sodium hydroxide solution had been added. A pH probe 155 monitored the pH of the mixture.

A controller 150 was interfaced to the flow meter 105 of the inlet water 90, and also to the chemical delivery diaphragm pumps 115 and 135. The controller 150 monitored the rate of die inlet water 90 and governed the rate at which the hydrogen peroxide-triacetin solution and the NaOH solution were introduced. If the flow of inlet water 90 decreased because of lower PAA requirements at the point-of-use 195, the rates at which the hydrogen peroxide-triacetin solution and the NaOH solution were pumped decreased accordingly. If the flow of inlet water 90 increased because of higher PAA requirements at the point-of-use 195, the rates at which the hydrogen peroxide-triacetin solution and the NaOH solution were pumped increased accordingly. If the flow of inlet water 90 stopped, pumps 115 and 135 stopped. Thus, the generation of PAA was both continuous and intermittent, and was tailored to the PAA requirements at the point-of-use.

The rate of the reaction between the hydrogen peroxide and the triacetin to form PAA is dependent upon the temperature of inlet water 90. If the temperature of inlet water 90 is high (for example, about 70° F.), the maximum conversion of triacetin into PAA may occur after 30 seconds, in which case the entire reaction medium was directed to the point-of-use 195. However, if the temperature of inlet water 90 is low (for example, about 32° F.), longer reaction times may be necessary to maximize the conversion of triacetin into PAA. Then, the reaction medium was directed through one or more residence chambers 165, 175, and 185 which also contained a packing material to promote turbulence and cause thorough mixing. Residence chambers 165, 175, and 185 were designed to be of volumes such that at a total flow rate of one gallon per minute, the reaction medium reached sampling port 170 in one minute, sampling port 180 in two minutes, and sampling port 190 in five minutes, to permit sampling at different time intervals.

Thus, depending on the temperature of the inlet water, the time to achieve the maximum conversion of hydrogen peroxide and triacetin into PAA was determined by sampling and analyzing the solution at sample ports 160, 170, 180, and 190. The entire flow was then directed from the sampling port with the highest amount of PAA to the point-of-use 195. In practice, the PAA generated from the reaction of hydrogen peroxide with triacetin is typically diluted at the point-of-use 195.

Point-of-use 195 may be recirculating cooling water; municipal wastewater; poultry chill tank water; water used to sanitize meat, poultry, or seafood products; fruit aid vegetable rinse water; or water used to clean and sanitize equipment used in the dairy, food, or beverage processing industries.

Example 14

Referring again to FIG. 1, a 55-gallon drum container 120 of a hydrogen peroxide-triacetin solution was prepared by mixing triacetin (251.5 lbs) with 50% hydrogen peroxide (298.4 lbs). The resulting 550 lbs of hydrogen peroxide-triacetin solution had a specific gravity of 1.19 g/mL (10 lbs/gal) and contained 54.3% hydrogen, peroxide and 45.7% triacetin. Thus, the mole ratio of hydrogen peroxide:triacetin was 3.8:1. The apparatus depicted in FIG. 1 was used to continuously and intermittently prepare an approximately 1% PAA solution.

Softened Local city water was directed through pressure regulator 100 at a flow rate of one gallon per minute as measured by flow meter 105. The container 120 of hydrogen peroxide-triacetin solution was equipped with a draw down tube so that the flow rate of the mixture could be measured. Diaphragm pump 115 injected the hydrogen peroxide-triacetin solution through injection quill 110. The hydrogen peroxide-triacetin solution was then mixed with the softened water using static mixer 125. A container 140 of 50% NaOH was also equipped with a draw down tube to measure the flow pumped by diaphragm pump 135 into injection quill 130.

The percent of PAA generated was measured by quenching samples drawn through the sampling ports in mineral acid, followed by use of the ceric sulfate-iodometric titration method. Table XVII summarizes the results of several trials where it was sought to maximize the conversion of triacetin into PAA and minimize the amount of 50% NaOH used.

TABLE XVII

| Trial # | Sample Port | % PAA Generated | % Triacetin Converted to PAA | Hydrogen Peroxide-Triacetin Mix Flow Rate (mL/min) | NaOH Flow Rate (mL/min) | pH (PAA solution) |
| --- | --- | --- | --- | --- | --- | --- |
| 1 | 160 | 1.083 | 65.42 | 115.73 | 112.11 | ~13 |
| 2 | 170 | 1.073 | 64.82 | 115.73 | 112.11 | 13.19 |
| 3 | 160 | 0.955 | 57.32 | 116.79 | 122.12 | 13.37 |
| 4 | 160 | 1.058 | 63.39 | 116.79 | 114.93 | 13.11 |
| 5 | 160 | 1.061 | 63.3 | 116.79 | 98.1 | 12.9 |
| 6 | 160 | 1.102 | 68.96 | 110.82 | 85.01 | 12.91 |
| 7 | 170 | 1.055 | 55.59 | 132.64 | 99.77 | 12.95 |
| 8 | 160 | 0.978 | 59.91 | 115.5 | 74 | 12.62 |
| 9 | 180 | 0.936 | 56.7 | 114.25 | 78 | 12.64 |

It can be seen that, the amount of PAA generated, and hence the conversion of triacetin into PAA, increased with the increasing flow rate of NaOH. For this mole ratio of hydrogen peroxide:triacetin of 3.8:1, the maximum amount of PAA was generated between 30 seconds (sample port 160) and two minutes (sample port 180) from the time the NaOH was added at injection quill 130. The flow rate of 74-78 mL/min of 50% NaOH was the optimum flow rate as it resulted in an efficient utilization of triacetin converted into PAA, consumed only a moderate amount of 50% NaOH, and had a lower pH that would have less impact on the pH of the receiving water.

Example 15

*E. coli* O157:H7 bacteria (ATCC 35150) was cultured in nutrient broth (Sigma, St. Louis, Mo.) by incubation for two days at 35° C. The bacteria were separated from the nutrient broth by centrifugation and carefully resuspended in two liters of sterile phosphate buffer, which was then split into two one-liter test solutions.

*Salmonella typhimurium* bacteria (ATCC 14028) was cultured in nutrient broth (Sigma, St Louis, Mo.) by incubation, for two days at 35° C. The bacteria were separated from the nutrient broth by centrifugation and carefully resuspended in two liters of sterile phosphate buffer, which was then split into two one-liter test solutions.

The amount of *E. coli* O157:H7 and *Salmonella typhimurium* bacteria were measured by serial dilution and plating on 3M *E. coli* plates and 3M *Enterobacteriaceae* Petrifilms, respectively.

A 1000 ppm stock of PAA was made by weighing 0.6386 g of Perasan MP-2 (5.83% hydrogen peroxide and 15.66% PAA) and adding water up to 100 g. Perasan MP-2 is an equilibrium product of PAA (Enviro Tech Chemical Services, Inc., Modesto, Calif.). Side-by-side, one of the *E. coli* and one of the *Salmonella* test solutions were treated with a nominal dose of 1.0 ppm PAA by adding one mL of the 1000 ppm PAA stock solution to each sample. After one minute, approximately 100 mL of each test solution was removed, and sodium thiosulfate (0.5 g) was added to neutralize the PAA and hydrogen peroxide oxidants. After five minutes, sodium thiosulfate (0.5 g) was added to the remaining test solution to neutralize the PAA and hydrogen peroxide in the rest of the test solutions. The amount of viable *E. coli* O157:H7 and *Salmonella typhimurium* bacteria remaining in the test solutions at the one-minute and five-minute contact times were measured by serial dilution and plating on 3M *E. coli* Petrifilms and 3M *Enterobacteriaceae*, respectively.

A 1% solution of PAA was prepared by combining 30.90 g of a mixture of 50% hydrogen peroxide and triacetin (54.22% hydrogen peroxide and 45.78% triacetin) with 929.4 g of water, and then adding 50% NaOH (40.53 g). The PAA solution had a pH of 12.79. The mole ratio of this mixture was 3.8:7.8:1 NaOH:hydrogen peroxide:triacetin. One minute after preparation, the second one-liter *E. coli* solution and the second one-liter *Salmonella* solution were treated with a nominal dose of 1.0 ppm PAA by adding 0.10 g of the 1% PAA solution to each sample. The test solution contact times, neutralization, and plating procedures were replicated for those that employed PAA from Perasan MP-2.

All 3M *E. coli* Petrifilms and 3M *Enterobacteriaceae* Petrifilms were incubated at 35° C. for 24 hours. After incubation, the plates were enumerated.

Table XVIII shows the microbiological results of the *E. coli* O157:H7 test solutions before treatment with PAA, one minute after the samples were dosed with a nominal 1.0 ppm PAA, and five minutes after being dosed with PAA. The *E. coli* test solution started with $\log_{10}$ 6.99 CFU/mL prior to being treated with 1.0 ppm of PAA from Perasan MP-2 or with 1 ppm of PAA from the 1% PAA solution.

The *E. coli* test solution treated with 1.0 ppm PAA from Perasan MP-2 contained a $\log_{10}$ 6.74 CFU/mL after one minute. This corresponds to 43.48% reduction. After five minutes, $\log_{10}$ 6.34 CFU/mL remained (77.50% reduction). The *E. coli* solution treated with a nominal 1.0 ppm PAA from the 1% PAA solution contained a $\log_{10}$ 6.78 CFU/mL after one minute and 6.63 CFU/mL after five minutes, respectively, corresponding to 38.02% and 56.12% reductions, respectively.

TABLE XVIII

*E. coli* O157:H7

| Description | $\log_{10}$ CFU/ml remaining | $\log_{10}$ reduction | % reduction |
|---|---|---|---|
| Control | 6.99 | N/A | N/A |
| Perasan MP-2 (1 min) | 6.74 | 0.25 | 43.48 |
| Perasan MP-2 (5 min) | 6.34 | 0.65 | 77.50 |
| 1% PAA solution (1 min) | 6.78 | 0.21 | 38.02 |
| 1% PAA solution (5 min) | 6.63 | 0.36 | 56.12 |

Table XIX shows the microbiological results of the *Salmonella typhimurium* test solutions before treatment with PAA, one minute after the samples were dosed with a nominal 1.0 ppm PAA, and five minutes after being dosed with PAA. The *Salmonella* test solution started with $\log_{10}$ 7.07 CFU/mL prior to being treated with PAA from Perasan MP-2 or with the 1% PAA solution.

The *Salmonella* solution treated with a nominal 1.0 ppm PAA from Perasan MP-2 contained a $\log_{10}$ 1.76 CFU/mL after one minute and 0.70 CFU/mL after five minutes, corresponding to >99.999% reduction at both contact times. The *Salmonella* test solution treated with 1.0 ppm PAA from the 1% PAA solution contained a $\log_{10}$ 6.69 CFU/mL after one minute. This corresponds to 58.31% reduction. After five minutes, $\log_{10}$ 4.95 CFU/mL remained (99.24% reduction).

TABLE XIX

*Salmonella typhimurium*

| Description | $\log_{10}$ CFU/ml remaining | $\log_{10}$ reduction | % reduction |
|---|---|---|---|
| Control | 7.07 | N/A | N/A |
| Perasan MP-2 (1 min) | 1.76 | 5.31 | 99.9995 |
| Perasan MP-2 (5 min) | 0.70 | 6.37 | >99.9999 |
| 1% PAA solution (1 min) | 6.69 | 0.38 | 58.31 |
| 1% PAA solution (5 min) | 4.95 | 2.12 | 99.24 |

The data in tables XVIII and XIX demonstrate that the 1% PAA had antimicrobial efficacy. After five minutes, the efficacy of this PAA was 99.24%, about equal to that of the Perasan MP-2, which was >99.9999%. The difference in efficacy at one minute was likely not of statistical significance, given that the comparison was only at the one-minute interval 5. Solid Compositions for Bleaching and Stain Removal A freely-flowable, solid peroxygen bleaching and stain removal composition comprises a liquid acetyl precursor, a water-soluble solid source of hydrogen peroxide, and a water-soluble solid source of alkalinity. A preferable liquid acetyl precursor is triacetin. The water soluble solid source of hydrogen peroxide is preferably sodium percarbonate, although sodium perborate monohydrate or sodium perborate tetrahydrate may be used. The water-soluble solid source of alkalinity acts as a pH control agent, and may be an alkali metal or earth alkali metal bicarbonate, carbonate, sesquicarbonate, borate, silicate, or hydroxide. Examples include sodium bicarbonate, sodium carbonate, sodium sesquicarbonate, sodium borate, sodium borate decahydrate (borax), sodium metasilicate, and sodium hydroxide.

In an embodiment, the composition comprises about 0.99% to about 8.45% triacetin, about 13% to about 54% sodium percarbonate, and about 24% to about 44% solid source of alkalinity.

The composition may optionally contain other components to improve performance. These components may prevent soil redeposition, sequester water hardness, increase dispercency, and lower surface tension.

Metal ions present in the bleaching medium can have a tendency to deposit on the substrates being bleached. Therefore, the solid bleaching composition may optionally contain a metal chelating agent such as a polyacrylate, a phosphonate, a maleic acid, a salt of ethylenediaminetetraacetic acid, a salt of nitrilotriacetic acid, or a salt of gluconic acid.

Surfactants reduce the surface tension of the bleaching medium and enhance the process of cleaning the soiled article. Surfactants also disperse the soil particles removed from the article and keep them suspended. Therefore, the solid bleaching composition may optionally contain a surfactant, such as an anionic, cationic, amphoteric, or non-ionic surfactant.

The solid bleaching composition may also optionally contain a solid zeolite, such as sodium zeolite, which acts to capture calcium and magnesium ions that may be present in the bleaching medium that would otherwise interact with an anionic surfactant, causing the surfactant to precipitate and removing it from the bleaching medium.

The composition may also optionally contain an inert, solid filler, such as anhydrous sodium sulfate, sodium, sulfate decahydrate, or sodium chloride. The filler increases the total ionic strength of the aqueous phase, but imparts no chemical properties to the bleaching medium.

To make the solid peroxygen bleaching and stain removal composition, the water soluble solid source of hydrogen peroxide, the water-soluble solid source of alkalinity, any chelating agent, any sufactant, and any filler are blended with the liquid triacetin to form a solid bleaching composition. The components may be added in any order. Any blending equipment may be used. Suitable examples of equipment include a ribbon and paddle blender, a V and double-cone blender, a Nauta screw mixer, and a rotating cement mixer. Alternatively, the ingredients may be blended by milling using a pulveriser mill, a ball mill, a hammer mill, a pin mill, an air mill, or a roller mill. Blending is performed for sufficient time to create a homogenous mixture. The mixture is a freely-flowable solid which is readily discharged from the blender.

Example 16

A series of tests were performed to determine whether triacetin, a liquid at room temperature, could be blended with a solid source of hydrogen peroxide to form a solid bleaching and stain removal composition that did not clump or turn into a sticky, non-flowable mass. The components listed in Table XX were mixed together to form a solid peroxygen bleach precursor.

TABLE XX

| Component | % |
| --- | --- |
| Sodium carbonate, anhydrous | 26.3 |
| Sodium percarbonate | 58.9 |

TABLE XX-continued

| Component | % |
| --- | --- |
| Sodium sulfate decahydrate | 13.8 |
| Surfactant (60% sodium dodecylbenzene sulfonate) | 1.0 |
| Total | 100 |

This solid peroxygen bleach precursor was then blended with incrementally increasing amounts of liquid triacetin. At each addition, the product was examined for flowability and for the odor of PAA. Table XXI summarizes the findings when up to 9.1 g of liquid triacetin was blended into 100 g of the solid peroxygen bleach precursor set forth above.

TABLE XXI

| Wt. of triacetin added to solid peroxygen bleach precursor (g) | Freely-flowable solid or sticky and clumping | Odor of PAA |
| --- | --- | --- |
| 1 | Freely- flowable solid | None |
| 2 | Freely- flowable solid | None |
| 3 | Freely- flowable solid | None |
| 4 | Freely- flowable solid | None |
| 5 | Freely- flowable solid | None |
| 6 | Freely- flowable solid | None |
| 7 | Freely- flowable solid | None |
| 8 | Freely- flowable solid | None |
| 8.45 | Freely-flowable solid | None |
| 9 | Sticky and clumping | None |
| 9.1 | Sticky and clumping | None |

Surprisingly, even though triacetin is a liquid, the solid peroxygen bleach precursor (100 g) could be blended with up to 8.45 g of the triacetin to form a freely-flowable solid composition, without becoming a sticky, non-flowable product which would not pour easily or would become a solid mass upon storage inside a container.

The solid peroxygen bleaching and stain removal composition was calculated to contain the following percentage of components, listed in Table XXII.

TABLE XXII

| Component | % |
| --- | --- |
| Sodium carbonate, anhydrous | 24.14 |
| Sodium percarbonate | 53.90 |
| Sodium sulfate decahydrate | 12.56 |
| Surfactant (90% sodium dodecylbenzene sulfonate) | 0.95 |
| Triacetin | 8.45 |
| Total | 100 |

Another unexpected result was that after storing the composition for over one year at ambient temperature, the composition still had not developed an odor of PAA.

These surprising results are in contest to the current belief that a liquid acetyl precursor, such as triacetin, could not be utilized with a solid source of hydrogen peroxide in a non-chlorine peroxygen bleaching and stain removal composition, for at least two reasons. First when a non-chlorine peroxygen bleaching composition is used in residential and commercial laundering applications, the product must be a freely-flowable solid. Typically, the acetyl precursor in a non-chlorinated peroxygen bleach is present in amounts up to 10%. It was believed that blending a liquid at this level with the other dry components of the laundry bleach would create a sticky, clumping mass, rather than, a freely-flowable solid, and would therefore not be acceptable to the user. Second, it was assumed that a liquid acetyl precursor would interact with the solid source of hydrogen peroxide and any free water or water of crystallization associated with other components, and thus form PAA in the product during storage, before being introduced to the aqueous bleaching medium. The high volatility and strong odor of the PAA would be unacceptable to the user of such a product.

Example 17

Two solid peroxygen bleaching and stain removal compositions were prepared with the components listed in Table XXIII.

TABLE XXIII

|  | % | Charge Weights, g |
|---|---|---|
| Components of Composition A |  |  |
| Premix 1 |  |  |
| Sodium Percarbonate | 13 | 195 |
| NANSA HS 90 | 1.5 | 22.5 |
| Sodium Metasilicate (Anhydrous) | 19.5 | 292.5 |
| Sodium Sulfate (Anhydrous) | 41 | 615 |
| Triacetin | 4 | 60 |
| Premix 2 |  |  |
| Mineral Oil | 1 | 15 |
| Sodium Hydroxide Beads | 4 | 60 |
| Soda Ash | 16 | 240 |
| Components of Composition B |  |  |
| Premix 1 |  |  |
| Sodium Percarbonate | 13 | 195 |
| NANSA HS 90 | 1.5 | 22.5 |
| Sodium Metasilicate (Anhydrous) | 19.5 | 292.5 |
| Sodium Sulfate (Anhydrous) | 43 | 645 |
| Triacetin | 4 | 60 |
| Premix 2 |  |  |
| Mineral Oil | 1 | 15 |
| Sodium Hydroxide Beads | 2 | 30 |
| Soda Ash | 16 | 240 |

In both cases, Premix 1 was prepared by kneading the NANSA HS 90 (a sodium dodecylbenzenesulfonate surfactant) with the sodium sulfate. The sodium sulfate helped break up the sticky surfactant efficiently. Then, the sodium percarbonate, the sodium metasilicate, and the triacetin were added and mixed by hand.

In both, cases. Premix 2 was prepared by mixing the sodium hydroxide beads with the mineral oil to afford a well-coated mixture, with some free-standing mineral oil remaining. Soda ash was blended in portions to take up the excess liquid and to provide a free-flowing solid mixture.

Premix 2 was blended in portions into Premix 1, and the final solid composition was mixed well by hand.

Both compositions A and B, which were held in uncovered bowls at ambient temperature after preparation, exhibited slow weight gain over time, most likely due to absorbance of water from the air. Each composition had gained 2.4% of its initial weight over a period of three days.

Neither composition exhibited significant exothermic behavior. However, composition A was hotter at the end of preparation and cooled more slowly than composition B. The temperature of composition A was 85° F. immediately after preparation, rose to 88° F. over the next ten minutes, and then fell slowly to 74° F. The temperature of composition B was 80° F. immediately after preparation, rose to 81° F. over the next twenty minutes, and then fell slowly to 65° F.

The solid peroxygen bleaching and stain removal composition described above may be used as follows.

First, the solid peroxygen, composition is introduced to an aqueous medium that is used for bleaching or stain removal of at least one article contained within the aqueous medium. For bleaching of laundry articles, about 5 g of bleaching composition is introduced for every liter of water used in the bleaching cycle. For home use, the bleaching composition can be added manually at the start of the wash. For commercial laundry systems, the bleaching composition may be introduced just before the bleaching cycle, toward the end of the wash and following the soil removal cycle. In most commercial and residential laundry machines, bleaching cycles are typically about 10-15 minutes.

Second, the composition is allowed to dissolve and react to form the bleaching medium containing PAA. The solid source of hydrogen peroxide, such as sodium percarbonate, and the solid source of alkalinity, such as sodium hydroxide, dissolve in the laundry water and cause the pH of the water to increase to above about 10.5.

While not wishing, to be bound by theory, it is believed that under elevated pH conditions, hydrogen peroxide dissociates according to the following equation:

$$H_2O_2 = H^+HO_2^-$$

The perhydroxyl anion ($HO_2^-$) then effects nucleophilic substitution reactions on the carbonyl groups of triacetin, in a perhydrolysis reaction, to form PAA and 1,2,3-propanetriol (glycerine). The laundry water would also contain unreacted hydrogen peroxide, unreacted triacetin, and sodium hydroxide.

Third, the aqueous solution of PAA and the unreacted hydrogen peroxide are mixed for sufficient time to effect bleaching or stain removal of the articles contained within the aqueous medium. Both commercial and residential bleaching cycles are about 10-15 minutes.

Fourth, the article is rinsed with fresh water so that it becomes substantially free of PAA and the unreacted hydrogen peroxide, the glycerine, the unreacted triacetin, and the sodium hydroxide. Generally, for a laundered article, the washing machine is programmed to empty the bleaching medium and replace it with fresh water. The machine can agitate the articles with the rinse water to enhance the rinsing process.

Fifth the article is allowed to dry. Any suitable means of drying the bleached articles may be employed. This includes the use of centrifugal forces to mechanically dewater the articles prior to introducing the wet articles to another machine before the articles are tumbled in a stream of hot air. Alternatively, the articles may be allowed to air dry without the use of externally-applied heat.

Example 18

Laundry swatches were made by cutting a tea towel into 50 equal 5×4 inch sheets. They were then separated into seven groups of seven swatches. Six of the groups were stained and the seventh group was left unstained for comparison purposes. Five of the groups that were stained were stained by soaking them in one of the following: black tea, black, coffee, red wine, blood (park), and acetone-extracted chlorophyll. The sixth group of swatches was stained by rubbing them on green grass. After allowing the stained swatches to dry, and before challenging the stains, the swatches were set aside for two months to allow the stains to set in the fabric.

A solid peroxygen bleaching and stain removal composition (200 g) was prepared by blending sodium percarbonate (104.0 g), triacetin (8.00 g), soda ash (80.01 g), and sodium, hydroxide beads (8.00 g). The final product was a freely-flowable solid.

The composition was tested using 1:100 dilution at both 75° F. and 104° F. The initial pH was measured and the concentrations of PAA and hydrogen peroxide were evaluated using the method of U.S. Pat. No. 7,651,724. At each temperature, the composition (1.0 g) was weighed out into a glass beaker (100 mL). To the beaker, city water (99 mL) was added while mixing on a stir plate. The pH and PAA generation profile was then monitored over the next 10-13 minutes to model the times of a typical low temperature and high temperature bleaching cycle. For city water at 75° F., the initial pH measured 11.2 and the PAA measured highest at 10.5 minutes (123 ppm PAA and 1594 ppm hydrogen peroxide). The test with city water at 104° F. had the same initial pH of 11.2, but the PAA measured highest at 5.5 minutes (133 ppm PAA and 1494 ppm $H_2O_2$). Table XXIV shows the amount of PAA generated and the amount of hydrogen peroxide remaining over time at 75° F. at a pH of 11.2. Table XXV shows the amount of PAA generated and the amount of hydrogen peroxide remaining over time at 104° F. at a pH of 11.2.

TABLE XXIV

| Time (min) | ppm PAA | ppm Hydrogen Peroxide |
|---|---|---|
| 1 | 61 | 1717 |
| 3 | 106 | 1673 |
| 5.2 | 113 | 1694 |
| 7.3 | 121 | 1571 |
| 10.5 | 123 | 1594 |
| 13.5 | 120 | 1547 |

TABLE XXV

| Time (min) | ppm PAA | ppm Hydrogen Peroxide |
|---|---|---|
| 0.5 | 72 | 1569 |
| 2.8 | 125 | 1426 |
| 5.5 | 133 | 1494 |
| 7.8 | 122 | 1427 |
| 10.3 | 119 | 1405 |

The stain removal ability of the composition was determined by comparing treated swatches to control swatches (swatches washed in just city water for the same amount of time and at elevated temperature) and non-stained swatches. The description of the swatches is set forth in Table XXVI. Three stained swatches were used for each test. The composition (10.0 g) was weighed, into a beaker (2000 mL). To this beaker a measured amount of hard water (990.0 g) was added at ambient temperature (64° F.). The swatches were added, to the solution and agitated by mixing with a plastic utensil for 10 minutes to simulate a laundry bleaching cycle. After 10 minutes, the wash water was discarded and a water rinse was performed by adding fresh city water (1000.0 g) to the swatches and agitating for two minutes using the same plastic utensil. The swatches were immediately removed thorn the beaker after rinsing, wrung out by hand, and laid to dry. These steps were then repeated using water at an elevated temperature (120° F.).

A control swatch was obtained by taking one swatch at a time from each stain group and washing in city water at an elevated temperature (120° F.) for 10 minutes in the same manner as the treated swatches. After the wash, the swatches were immediately removed, wrung out by hand, and laid to dry.

TABLE XXVI

| Type of Swatches | Description |
|---|---|
| Treated Swatches | Swatches subjected to bleaching for 10 minutes using bleaching formulation with triacetin and a 2-minute rinse with hard water |
| Control Swatches | Swatches subjected to only an elevated temperature (120° F.) hard water wash for 10 minutes |
| Non-Stained Swatches | Non-altered swatches |

The bleaching ability of the test swatches was obtained by visual comparison of the treated swatches to the control swatches (treated with water only) and the non-stained swatches. The scale of bleaching ability of the composition was rated on a scale of 0 to 10, with 0 representing no apparent bleaching or stain removal properties of the swatches compared to the control and 10 representing bleaching of swatches to the original color (i.e., identical to the non-stained swatches). Three individuals rated, the bleaching ability of the triacetin-containing formulation on the swatches independently. The average ratings from the three individuals are shown in Table XXVII.

TABLE XXVII

| Type of Stain | Bleaching Formula at 64° F. | Bleaching Formula at 120° F. |
|---|---|---|
| Black Tea | 5 | 8 |
| Black Coffee | 2 | 8 |
| Red Wine | 3 | 7 |
| Blood (pork) | 3 | 3 |
| Extracted chlorophyll | 0 | 0 |
| Grass Stains | 0 | 1 | it can be seen that, in general, the composition displayed enhanced stain removal properties at elevated temperature. Excellent stain removal, properties were obtained for black tea and black coffee, and more moderate performance with red wine and blood. The composition had virtually no effect on grass stains or the chlorophyll pigment that was acetone-extracted from green grass.

The invention has been described above with the reference to the preferred embodiments. Those skilled in the art may envision other embodiments and variations of the invention that fall within the scope of the claims.

We claim:

1. A method of generating a non-equilibrium solution of peracetic acid, comprising:
   a. providing water;
   b. introducing triacetin and aqueous hydrogen peroxide to the water;
   c. mixing the triacetin and the aqueous hydrogen peroxide with the water to form a mixture;
   d. adding an aqueous source of an alkali metal or earth alkali metal hydroxide to the mixture; and
   e. forming a reaction medium comprising a non-equilibrium solution of peracetic acid.

2. The method of claim 1, wherein the triacetin and the aqueous hydrogen peroxide are introduced simultaneously.

3. The method of claim 1, wherein the triacetin and the aqueous hydrogen peroxide are introduced sequentially with either one first.

4. The method of claim 1, wherein the provided water is an aqueous stream.

5. The method of claim 1, wherein the provided water is contained in a mixing tank or other vessel.

6. The method of claim 1, wherein the aqueous source of the alkali metal or earth alkali metal hydroxide is sodium hydroxide.

7. The method of claim 6, wherein, the sodium hydroxide is about 1.82% to about 7.28%.

8. The method of claim 1, wherein step (d) is performed simultaneously with step (b).

9. The method of claim 1, further comprising allowing the reaction medium sufficient time to maximize the conversion of the hydrogen peroxide and the triacetin into peracetic acid.

10. The method of claim 9, wherein the time to maximize the conversion of the hydrogen peroxide and the triacetin into peracetic acid is about 30 seconds to about five minutes.

11. The method of claim 10, wherein the percent of triacetin that is converted into peracetic acid is about 40.9% to about 85.7%.

12. The method of claim 6, wherein the mole ratio of the sodium hydroxide to the hydrogen peroxide to the triacetin is about 4.2:3.8:1.

13. The method of claim 1, wherein said steps (a) through (e) are performed on a continuous basis.

14. The method of claim 1, wherein said steps (a) through (e) are performed on an intermittent basis.

* * * * *